United States Patent
Sato et al.

(10) Patent No.: US 7,671,117 B2
(45) Date of Patent: Mar. 2, 2010

(54) RESIN COMPOSITION

(75) Inventors: Noritaka Sato, Kanagawa (JP);
Tsutomu Noguchi, Kanagawa (JP);
Hiroyuki Mori, Kanagawa (JP)

(73) Assignee: Sony Corporation, Tokyo (JP)

( * ) Notice: Subject to any disclaimer, the term of this patent is extended or adjusted under 35 U.S.C. 154(b) by 122 days.

(21) Appl. No.: 11/830,276

(22) Filed: Jul. 30, 2007

(65) Prior Publication Data

US 2009/0005475 A1   Jan. 1, 2009

Related U.S. Application Data

(62) Division of application No. 10/494,007, filed as application No. PCT/JP03/11397 on Sep. 5, 2003, now abandoned.

(30) Foreign Application Priority Data

Sep. 9, 2002   (JP)   ............... 2002-263279
Sep. 9, 2002   (JP)   ............... 2002-263283

(51) Int. Cl.
*C07D 209/48* (2006.01)
*C08K 5/00* (2006.01)

(52) U.S. Cl. .................. 524/94; 106/494

(58) Field of Classification Search ........... 524/94
See application file for complete search history.

(56) References Cited

U.S. PATENT DOCUMENTS

| | | | |
|---|---|---|---|
| 4,814,366 A * | 3/1989 | Hirahara et al. | ........ 524/89 |
| 5,554,217 A | 9/1996 | Babler | |
| 6,093,791 A | 7/2000 | Gruber | |
| 6,121,410 A | 9/2000 | Gruber | |
| 7,285,589 B2 * | 10/2007 | Fujihira et al. | ........ 524/442 |

FOREIGN PATENT DOCUMENTS

| | | |
|---|---|---|
| EP | 0816440 | 1/1998 |
| EP | 1106656 | 6/2001 |
| EP | 0765913 | 4/2002 |
| EP | 123214 | 8/2002 |
| JP | 1980-023198 | 2/1980 |
| JP | 1980-160058 | 12/1980 |
| JP | 63-044653 | 2/1988 |
| JP | 1992-235185 | 8/1992 |
| JP | 1999-148024 | 6/1999 |
| JP | 11-322949 | 11/1999 |
| JP | 1999-322949 | 11/1999 |
| JP | 2000-302986 | 10/2000 |
| WO | WO0153799 | 7/2001 |
| WO | WO2004009787 | 1/2004 |

OTHER PUBLICATIONS

EP Communication dated Sep. 29, 2008 for Application No. 03792746.4-1213.
Washizu M., et al.: "Applications of Electrostatic Stretch-And-Positioning of DNA" IEEE Transnactions on Industry Applications vol. 31, 1995, pp. 447-456, XP000537471.
Office Action for Japanese Application No. 2004-534185 dated Aug. 7, 2009.

* cited by examiner

*Primary Examiner*—Ling-Siu Choi
*Assistant Examiner*—Hui Chin
(74) *Attorney, Agent, or Firm*—Sonnenschein Nath & Rosenthal LLP

(57) ABSTRACT

Moldings made with a polyester resin which comprises a cyclic compound represented by a following formula

A1-B-A2

(in the formula, A1 and A2 are the same or different and show groups represented by a below-described formula,

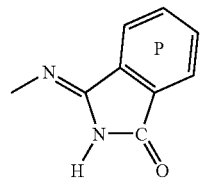

P shows a benzene ring which may be replaced by a material, and B shows a bivalent hydrocarbon group which may be replaced by a material) and polyester capable of having a crystal structure.

6 Claims, 1 Drawing Sheet

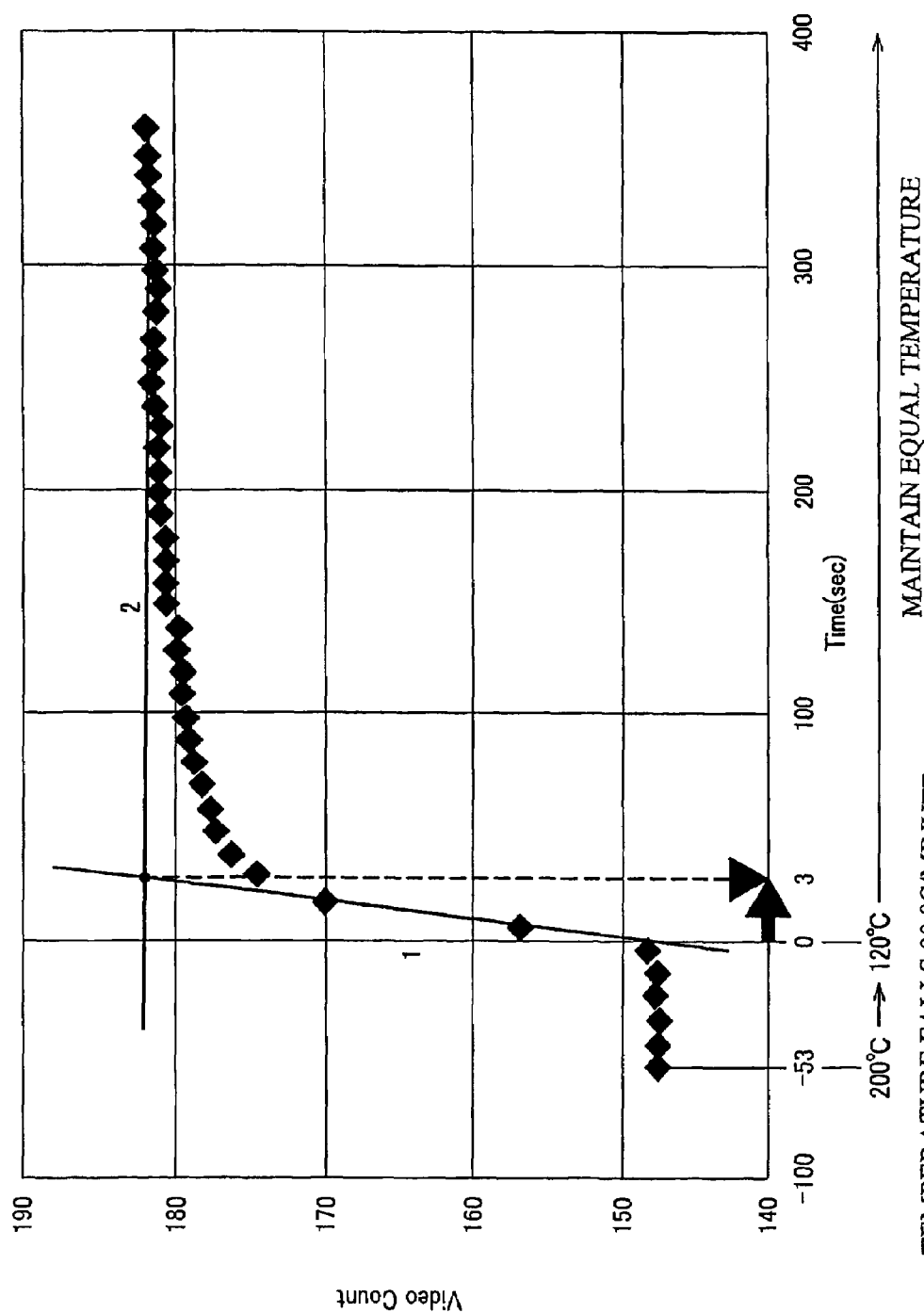

RESIN COMPOSITION

RELATED APPLICATION DATA

This application is a divisional of U.S. patent application Ser. No. 10/494,007, filed Apr. 29, 2004, the entirety of which is incorporated herein by reference to the extent permitted by law. application Ser. No. 10/494,007 is the Section 371 National Stage of PCT/JP03/11397. The present application claims priority to Japanese Patent Application No. 2002-263279 and Japanese Patent Application No. 2002-263283 filed in the Japanese Patent Office on Sep. 9, 2002, the entirety both of which also are incorporated by reference herein to the extent permitted by law.

BACKGROUND

The present invention relates to, a resin component, a resin component for molding and a method for producing it, and more particularly to a resin component for molding including a biodegradable resin and a method for producing it.

In the field of a resin component and a resin component for molding, a biodegradable resin decomposed in a natural atmosphere and the moldings thereof have been hitherto required in view of natural atmospheric protection. The biodegradable resin such as an aliphatic polyester has been especially vigorously studied. Specially, polylactic acid ordinarily has a high melting point (170 to 180° C.) and the moldings made of the polylactic acid are ordinarily transparent and they have commenced to be put into practice depending on their uses. Generally, the moldings made of the polylactic acid are poor in their heat resistance and have glass transition temperature (Tg) of about 60° C. Accordingly, the moldings made of the polylactic acid are disadvantageously deformed when the temperature exceeds the above-described temperature. In the use of the casing of an electric product or a structural material, a heat resistance to the temperature of about 80° C. is required. Therefore, to utilize the moldings for uses requiring the heat resistance, various kinds of investigations have been carried out. The heat resistance referred to in this specification means a sufficiently high rigidity (modulus of elasticity) at about 80° C. as high as 100 MPa.

To increase the heat resistance of biodegradable polyester, for instance, the addition of inorganic filler has been studied. As the inorganic filler, talc or mica or the like having the heat resistance has been studied. For the purpose of improving mechanical characteristics and hardening a resin, a hard inorganic filler having the heat resistance is added to the resin, like what is called reinforcing steel embedded in concrete. However, the mechanical characteristics are imperfectly improved only by adding the inorganic filler to the resin.

The polylactic acid as a typical example of the biodegradable polyester is a polymer capable of having a crystal structure. However, since the moldings of the polylactic acid is ordinarily amorphous, the moldings are apt to be thermally deformed. Thus, a proposal has been provided that the polylactic acid is crystallized and hardened under a heat treatment, for instance, during molding or after molding to improve the heat resistance. When the polylactic acid is crystallized in such a method, it takes extremely much time to crystallize the polylactic acid. For example, a molding cycle of about one minute is ordinarily required in an injection molding. However, it unrealistically takes too much time to completely crystallize the moldings of the polylactic acid in a die. When the polylactic acid is crystallized in such a method, the size of a crystal is of the order of micron to of the order of sub mm. Thus, the crystals themselves of the polylactic acid inconveniently cause a factor of light scattering to become thick in white, so that a transparency is lost. In order to solve these problems, that is, to accelerate the crystallization, the addition of, what is called a nucleus agent begins to be studied.

The nucleus agent forms a primary crystal nucleus of a crystalline polymer to accelerate the growth of the crystal of the crystalline polymer. Further, in a broad sense, the nucleus agent may be regarded as a material for accelerating the crystallization of the crystalline polymer. That is, a material for accelerating the crystallization speed of the polymer may be regarded as a nucleus agent. When the nucleus agent such as the former is added to a resin, the crystals of the polymer become fine, so that the rigidity of the resin is improved or the transparency is improved. Otherwise, when the polymer is crystallized during molding, the entire speed (time) of the crystallization is accelerated. Thus, a molding cycle can be advantageously shortened.

The above-described effects can be exhibited in other crystalline resins as examples. For example, in polypropylene (abbreviate it as PP, hereinafter), the nucleus agent is added thereto, so that the rigidity or the transparency thereof is improved. Nowadays, the PP whose materiality is improved has been put into practical use in many moldings. The nucleus agent includes, for instance, a sorbitol material and its operational function is not completely clarified. However, a three-dimensional network formed by this material is considered to effectively operate. Further, a nucleus agent of metal salt type is also put into practical use for the PP. As such a nucleus agent, for instance, hydroxy-di (t-butyl benzoate) aluminum, sodium bis(4-t-butylphenyl) phosphate, or sodium methylene bis(2,4-di-t-butylphenyl) phosphate, etc. may be exemplified.

However, few effective nucleus agents have been found for aliphatic polyester such as polylactic acid. The above-described talc functions also as a nucleus agent. Talc may seem to be used as an effective nucleus agent depending on its use. In case talc is used as the nucleus agent, when an amount of addition thereof is not several ten %, a satisfactory effect cannot be obtained. Furthermore, when the amount of addition of talc is increased, the component of the resin inconveniently becomes brittle. In such an amount of addition, the component of the resin becomes white and the transparency thereof cannot be absolutely expected.

Even in the aliphatic polyester, the nucleus agent for accelerating the crystallization has been studied so far. For example, as the nucleus agent for accelerating the crystallization, the use of sorbitol material is disclosed in Japanese Patent Application Laid-Open No. hei 10-158369. This publication discloses that the sorbitol material has satisfactory results as a nucleus agent for crystallization in the PP and the sorbitol material is added to polylactic acid to effectively act thereon. In addition thereto, methods for adding a nucleus agent to polyester to accelerate the crystallization thereof are disclosed in Japanese Patent Application Laid-Open No. hei 9-278991, Japanese Patent Application laid-Open No. hei 11-5849 and Japanese patent Application Laid-Open No. hei 11-116783.

However, any of the techniques has not been put into practical use.

DISCLOSURE OF THE INVENTION

It is an object of the present invention to provide a new resin component, a resin component for molding and a method for producing it that can solve the above-described problems of the prior art.

It is another object of the present invention to provide a resin component for molding to which a nucleus agent suitable for accelerating the crystallization of polyesters having crystal structures, especially, biodegradable polyester among them is added.

It is a still another object of the present invention to provide the moldings including a resin component whose crystallization is improved.

The inventors of the present invention eagerly studied to achieve the above-described objects. Thus, they found that a cyclic compound represented by a following formula

A1-B-A2 was added to polyester capable of having a crystal structure (in the formula, A1 and A2 are the same or different and show groups represented by a below-described formula,

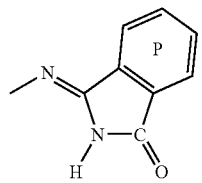

P shows a benzene ring which may be replaced by a material, and B shows a bivalent hydrocarbon group which may be replaced by a material.) to accelerate the crystallization thereof.

Here, the inventors recognized that the cyclic compound was preferably an isoindolinone compound. More specifically, they had a knowledge that the cyclic compound was more preferably 3,3'-(2-methyl-1,3-phenylene) diimino-bis-4,5,6,7-tetrachloro-1H-isoindole-1-one (Pigment Yellow 109) or 3,3'-(1,4-phenylene diimino) bis-4,5,6,7-tetrachloro-1H-isoindole-1-one (Pigment Yellow 110). Further, they found that the particle diameter of the cyclic compound was preferably 10 μm or smaller, more preferably 1 μm or smaller and most preferably 0.1 μm or smaller. Further, they recognized that the amount of addition of the cyclic compound to the resin component was preferably located within a range of 0.001 to 10 parts by weight relative to polyester of 100 parts by weight capable of having a crystal structure, and more preferably located within a range of 0.01 to 1 parts by weight.

The inventors of the present invention understood that the polyester capable of the crystal structure was suitably biodegradable polyester, and further, polylactic acid was preferable in the biodegradable polyester. Further, they found that inorganic filler, preferably talc was added to the polyester in addition to the cyclic compound to accelerate the crystallization of the polyester without canceling their effects with each other. They understood that the amount of addition of the inorganic filler was suitably located within 1 to 50 parts by weight relative to the polyester of 100 parts by weight capable of having the crystal structure. Further, they found that a hydrolysis inhibitor was added to the resin component for molding so that the hydrolysis of the polyester could be suppressed without lowering its crystalline property. The inventors found that as the hydrolysis inhibitor, a compound having a carbodiimide group was suitable. They understood that the resin component preferably had a crystallization factor located within a range of 40 to 100%, preferably had crystallization time located within a range of 0 to 200 seconds and preferably had a modulus of elasticity at 80° C. located within a range of 50 to 5000 MPa.

Further, the inventors of the present invention found that the crystallization of the resin component for molding according to the present invention was accelerated and the rigidity of the moldings formed by using it was improved so that the resin component for molding was suitable for forming the moldings. They found that the moldings were preferably casings of electric or electronic devices.

Further, the inventors found that the cyclic compound represented by a following formula

A1-B-A2

(in the formula, A1 and A2 are the same or different and show groups represented by a below-described formula,

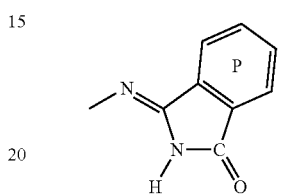

P shows a benzene ring which may be replaced by a material, and B shows a bivalent hydrocarbon group which may be replaced by a material) was mixed with polyester capable of having the crystal structure, and then, the mixture was heated and kneaded to produce the resin component whose crystallization was improved.

Further, the inventors found that a nucleus agent including the cyclic compound represented by a following formula

A1-B-A2

(in the formula, A1 and A2 are the same or different and show groups represented by a below-described formula,

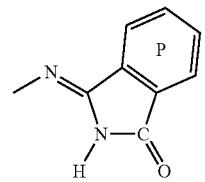

P shows a benzene ring which may be replaced by a material, and B shows a bivalent hydrocarbon group which may be replaced by a material) outstandingly accelerated the crystallization of the polyester capable of having the crystal structure. Thus, they found that the above-described cyclic compound could be used as the nucleus agent for the polyester capable of having the crystal structure.

After the inventors of the present invention obtained various kinds of knowledge, they continuously studied to complete the present invention.

Specifically, the present invention concerns a resin component with its crystallization improved comprising: a cyclic compound represented by a following formula

A1-B-A2

(in the formula, A1 and A2 are the same or different and show groups represented by a below-described formula,

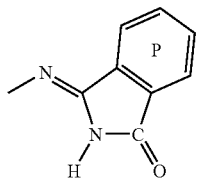

P shows a benzene ring which may be replaced by a material, and B shows a bivalent hydrocarbon group which may be replaced by a material) and polyester capable of having a crystal structure.

As the cyclic compound forming the resin component according to the present invention, 3,3'-(2-methyl-1,3-phenylene) diimino-bis-4,5,6,7-tetrachloro-1H-isoindole-1-one (Pigment Yellow 109) or 3,3'-(1,4-phenylene diimino) bis-4,5,6,7-tetrachloro-1H-isoindole-1-one (Pigment Yellow 110) is used.

The cyclic compound is preferably a particle whose particle diameter is 10 μm or smaller.

In the present invention, the polyester capable of having the crystal structure is biodegradable polyester and the biodegradable polyester is polylactic acid.

The resin component according to the present invention is used as a resin molding material.

In the resin component according to the present invention, the mixing ratio of the cyclic compound is located within a range of 0.001 to 10 parts by weight relative to the polyester capable of having the crystal structure of 100 parts by weight.

In the resin component according to the present invention, the mixing ratio of the cyclic compound is located within a range of 0.01 to 1 parts by weight relative to the polyester capable of having the crystal structure of 100 parts by weight.

To the resin component according to the present invention, inorganic filler is further added. As the inorganic filler, talc can be used.

Here, the mixing ratio of the inorganic filler is located within a range of 1 to 50 parts by weight relative to the resin component of 100 parts by weight.

Further, a hydrolysis inhibitor is further included in the resin component according to the present invention. The hydrolysis inhibitor includes a compound having a carbodiimide group.

In the resin component according to the present invention, the crystallization rate is located within a range of 40 to 100% and crystallization time is located within a range of 0 to 200 seconds.

In the resin component according to the present invention, modulus of elasticity at 80° C. is located within a range of 50 to 5000 MPa.

The present invention concerns the moldings made of a resin and the moldings is made of the resin component with its crystallization improved comprising: a cyclic compound represented by a following formula

A1-B-A2

(in the formula, A1 and A2 are the same or different and show groups represented by a below-described formula,

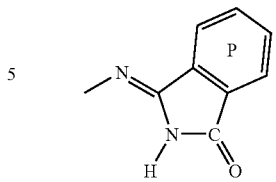

P shows a benzene ring which may be replaced by a material, and B shows a bivalent hydrocarbon group which may be replaced by a material) and polyester capable of having a crystal structure.

The present invention concerns casings of electric and electronic devices. The casings are made of the resin component with its crystallization improved comprising: a cyclic compound represented by a following formula

A1-B-A2

(in the formula, A1 and A2 are the same or different and show groups represented by a below-described formula,

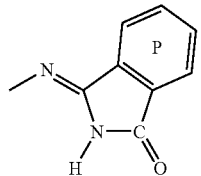

P shows a benzene ring which may be replaced by a material, and B shows a bivalent hydrocarbon group which may be replaced by a material) and polyester capable of having a crystal structure.

The present invention concerns a method for producing a resin component comprising the steps of: mixing a cyclic compound represented by a following formula

A1-B-A2

(in the formula, A1 and A2 are the same or different and show groups represented by a below-described formula,

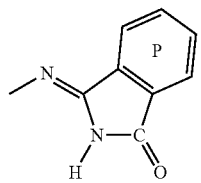

P shows a benzene ring which may be replaced by a material, and B shows a bivalent hydrocarbon group which may be replaced by a material) with polyester capable of having a crystal structure and heating and kneading the mixture.

The present invention concerns a nucleus agent for polyester capable of having a crystal structure which is represented by a following formula

A1-B-A2

(in the formula, A1 and A2 are the same or different and show groups represented by a below-described formula,

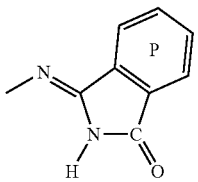

P shows a benzene ring which may be replaced by a material, and B shows a bivalent hydrocarbon group which may be replaced by a material).

Further, the inventors of the present invention eagerly studied to achieve the above-described objects. As a result, they found that one or more cyclic compounds selected from between a copper phthalocyanine crystal (a) which might be replaced by a material, a phthalocyanine compound (b) which might include one kind of metal selected from between zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium which might be replaced by a material, and a porphyrin compound (c) which might be replaced by a material were added to polyester capable of having a crystal structure to accelerate the crystallization of the polyester.

Here, the inventors of the present invention understood that the cyclic compound was preferably a copper phthalocyanine crystal, a chlorophyll compound or a haemin compound. They found that the copper phthalocyanine crystal was preferably a beta type or an epsilon type crystal. Further, they found that the cyclic compound was a particle whose particle diameter was 10 μm or smaller.

Further, the inventors of the present invention found that the polyester capable of having the crystal structure was preferably biodegradable polyester, the biodegradable polyester was preferably polylactic acid and the resin component was preferably used for molding. Further, they found that the amount of addition of the cyclic compound for the resin component was suitably located within a range of 0.001 to 10 parts by weight relative to the polyester capable of having the crystal structure of 100 parts by weight and preferably located within a range of 0.01 to 1 parts by weight.

The inventors of the present invention found that in the resin component according to the present invention, inorganic filler, preferably talc, as well as the cyclic compound was added to the polyester so that the crystallization of the polyester could be accelerated without canceling their effects with each other. They found that the amount of addition of the inorganic filler was suitably located within a range of 1 to 50 parts by weight relative to the polyester capable of having the crystal structure of 100 parts by weight. They found that a hydrolysis inhibitor was further added to the resin component for molding to suppress the hydrolysis of the polyester without lowering its crystallization. They found that the hydrolysis inhibitor suitably included a compound having a carbodiimide group. They found that in the resin component, the crystallization rate was preferably located within a range of 40 to 100%, crystallization time was preferably located within a range of 0 to 200 seconds and modulus of elasticity at 80° C. was preferably located within a range of 50 to 5000 MPa.

Further, the inventors of the present invention recognized that the resin component for molding according to the present invention had its crystallization improved, the moldings formed by using it had rigidity improved and the resin component was suitable for producing the moldings. They found that the moldings were preferably the casings of electric or electronic devices.

The inventors of the present invention found that when the resin component of the present invention was produced, the resin component could be produced by mixing one or more cyclic compounds selected from between a copper phthalocyanine crystal (a) which might be replaced by a material, a phthalocyanine compound (b) which might include one kind of metal selected from between zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium which might be replaced by a material, and a porphyrin compound (c) which might may be replaced by a material with polyester capable of having a crystal structure, and heating and kneading the mixture.

The inventors of the present invention further recognized that in order to accelerate the crystallization of the polyester, a nucleus agent was effectively used which comprised one or more cyclic compounds selected from between a copper phthalocyanine crystal (a) which might be replaced by a material, a phthalocyanine compound (b) which might include one kind of metal selected from between zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium which might be replaced by a material, and a porphyrin compound (c) which might be replaced by a material. They found that the cyclic compound could be used as the nucleus agent for polyester capable of having the crystal structure.

Still another objects of the present invention and specific advantages obtained by the present invention will be more apparent from the description of embodiments explained by referring to the drawings.

BRIEF DESCRIPTION OF THE DRAWINGS

FIG. 1 is a diagram showing a graph of luminance and time and showing a way to obtain crystallization time.

BEST MODE FOR CARRYING OUT THE INVENTION

Now, a resin component, a resin component for molding and a method for producing it according to the present invention will be more specifically described.

A resin component according to the present invention is a resin component whose crystallization is improved that comprises a cyclic compound represented by a following formula

A1-B-A2

(in the formula, A1 and A2 are the same or different and show groups represented by a below-described formula,

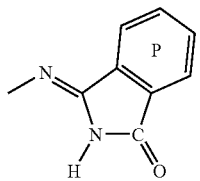

P shows a benzene ring which may be replaced by a material, and B shows a bivalent hydrocarbon group which may be replaced by a material) and polyester capable of having a crystal structure.

Now, each of constituents will be described below.

As the cyclic compound used in the present invention, any of cyclic compounds represented by a following formula

A1-B-A2

(in the formula, A1 and A2 are the same or different and show groups represented by a below-described formula,

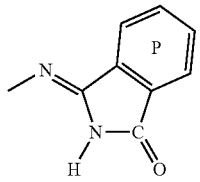

P shows a benzene ring which may be replaced by a material, and B shows a bivalent hydrocarbon group which may be replaced by a material) may be employed. Well-known cyclic compounds may be used.

As "a benzene ring which may be replaced by a material", for instance, a benzene ring which is replaced by the one to four same or different substituent groups or a benzene ring which is not replaced by the substituent groups or the like may be exemplified. As the substituent groups, such substituent groups as described below may be exemplified. They include, for instance, halogen atoms (for instance, fluorine, bromine, iodine, etc.), nitro groups, cyano groups, hydroxy groups, thiol groups, sulfo groups, sulfino groups, mercapto groups, phosphono groups, alkyl groups (for instance, methyl groups, ethyl groups, isopropyl groups, n-propyl groups, n-butyl groups, isobutyl groups, secondary butyl groups, tertiary butyl groups or various kinds of other isomers such as pentyl groups, hexyl groups, heptyl groups, octyl groups, nonyl groups, decyl groups, undecyl groups, dodecyl groups, tridecyl groups, tetradecyl groups, pentadecyl groups, hexadecyl groups, heptadecyl groups, octadecyl groups, nonadecyl groups, eicosyl groups, etc.), hydroxy alkyl groups (for instance, hydroxy methyl groups, hydroxy ethyl groups, 1-hydroxy isopropyl groups, 1-hydroxy-n-propyl groups, 2-hydroxy-n-butyl groups, 1-hydroxy-isobutyl groups, 1-hydroxy-secondary butyl groups, 1-hydroxy-tertiary butyl groups, etc.), halogenoalkyl groups (for instance, chloromethyl, dichloromethyl, trichloromethyl, fluoromethyl, difluoromethyl, trifluoromethyl, 2-bromoethyl, 2,2,2-trifluoroethyl, pentafluoro ethyl, 3,3,3-trifluoro propyl, 4,4,4-trifluoro butyl, 5,5,5-trifluoro pentyl, 6,6,6-trifluoro hexyl, etc.), cycloalkyl groups (for instance, cyclopropyl, cyclobutyl, cyclopentyl, cyclohexyl, cycloheptyl, etc.), alkenyl groups (for instance, vinyl, crotyl, 2-pentenyl, 3-hexenyl, etc.), cycloalkenyl groups (for instance, 2-cyclopentenyl, 2-cyclohexenyl, 2-cyclopentenyl methyl, cyclohexenyl methyl, etc.), alkynyl groups (for instance, ethynyl, 1-propynyl, 2-propynyl, 1-butynyl, 2-pentynyl, 3-hexynyl, etc.), oxo groups, thioxo groups, amidino groups, imino groups, alkylenedioxy groups (for instance, methylenedioxy, ethylenedioxy, etc.), alkoxy groups (for instance, methoxy, ethoxy, propoxy, isopropoxy, butoxy, isobutoxy, sec-butoxy, tert-butoxy, pentyloxy, neopentyloxy, hexyloxy, etc.), alkylthio groups (for instance, methylthio, ethylthio, propylthio, isopropylthio, butylthio, isobutylthio, pentylthio, hexylthio, etc.), carboxyl groups, alkanoyl groups (for instance, formyl; acetyl, propionyl, butyryl, isobutyryl, etc.), alkanoyloxy groups (for instance, formyloxy; alkyl-carbonyloxy groups such as acetyloxy, propionyloxy, butyryloxy, isobutyryloxy, etc.), alkoxy carbonyl groups (for instance, methoxy carbonyl, ethoxy carbonyl, propoxy carbonyl, butoxy carbonyl, etc.), aralkyloxy carbonyl groups (for instance, benzyloxy carbonyl, etc.), thiocarbamoyl groups, alkyl sulfinyl groups (for instance, methyl sulfinyl, ethyl sulfinyl, etc.), alkyl sulfonyl groups (for instance, methyl sulfonyl, ethyl sulfonyl, butyl sulfonyl, etc), sulfamoyl groups, mono-alkyl sulfamoyl groups (for instance, methyl sulfamoyl, ethyl sulfamoyl, etc.), di-alkyl sulfamoyl groups (for instance, dimethyl sulfamoyl, diethyl sulfamoyl, etc.), allyl sulfamoyl groups (for instance, phenyl sulfamoyl, naphthyl sulfamoyl, etc.), allyl groups (for instance, phenyl, naphthyl, etc.), allyloxy groups (for instance, phenyloxy, naphthyloxy, etc.), allylthio groups (for instance, phenylthio, naphthylthio, etc.), allyl sulfinyl groups (for instance, phenyl sulfinyl, naphthyl sulfinyl, etc.), allyl sulfonyl groups (for instance, phenyl sulfonyl, naphthyl sulfonyl, etc.), allyl carbonyl groups (for instance, benzoyl, naphthoyl, etc.), allyl carbonyloxy groups (for instance, benzoyloxy, naphthoyloxy, etc.), alkyl carbonyl amino groups which may be halogenated (for instance, acetyl amino, trifluoro acetyl amino, etc.), carbamoyl groups which may have substituent groups (for instance, groups represented by a formula —CONR3R4 (in the formula, R3 and R4 respectively show hydrogen atoms, hydrocarbon groups which may have substituent groups or heterocyclic groups which may have substituent groups, or R3 and R4 may form a ring with an adjacent nitrogen atom.)), amino groups which may have substituent groups (for instance, amino, alkyl amino, tetrahydro pyrrole, piperazine, piperidine, morpholine, thiomorpholine, pyrrole, imidazole, etc.), ureido groups which may have substituent groups (for instance, groups represented by a formula —NHCONR3R4 (in the formula, R3 and R4 show the same meanings as described above) or the like)), carboxamide groups which may have substituent groups (for instance, groups represented by a formula —NR3COR4 (in the formula, R3 and R4 show the same meanings as described above)), sulfonamide groups which may have substituent groups (for instance, groups represented by a formula —NR3SO2R4 (in the formula, R3 and R4 show the same meanings as described above), etc.), heterocyclic groups which may have substituent groups (for instance, aromatic heterocyclic groups including at least one of one to three kinds of hetero atoms selected from oxygen atoms, sulfur atoms and nitrogen atoms as well as carbon atoms as atoms (annular atoms) forming a cyclic system, saturated or unsaturated aliphatic heterocyclic groups, etc.) or substituent groups obtained by replacing these substituent groups by materials as much as chemically permissible.

As "a bivalent hydrocarbon group which may be replaced by a material", for example, a bivalent hydrocarbon group which is replaced by one or more same or different substituent groups or a bivalent hydrocarbon group which is not replaced by the substituent groups may be exemplified. Here, the substituent groups have the same meanings as described above.

As the bivalent hydrocarbon groups, such hydrocarbon groups as described below may be enumerated. They include, for example, alkylene groups (for instance, methylene, methyl methylene, dimethyl methylene, ethylene, propylene, trimethylene, tetramethylene, pentamethylene, hexamethylene, heptamethylene, octamethylene, butylene groups, 2-methyl propylene groups, pentamethylene groups, pentylene groups, 2-methyl tetramethylene groups, 2,2-dimethyl trimethylene groups, 2-ethyl trimethylene groups, hexamethylene groups, hexylene groups, 2-methyl pentamethylene groups, 3-methyl pentamethylene groups, heptamethylene groups, heptylene groups, octamethylene groups, octylene groups, 2-ethyl hexylene groups, nonamethylene groups, nonylene groups, decamethylene groups, decylene groups, cyclopropylene, 1,2-cyclobutylene, 1,3-cyclobutylene, cyclopentylene, 1,3-cyclopentylene, cyclohexylene, 1,3-cyclohexylene, 1,4-cyclohexylene, etc.), alkenylene groups (for instance, vinylene, propenylene, 1-propene-1,2-ylene, 2-propene-1,2-ylene, butenylene (for instance, 1-butene-1,4-ylene, 2-butene-1,4-ylene, etc.), pentenylene (for instance, 1-pentene-1,5-ylene, 2-pentene-1,5-ylene, etc.), hexenylene (for instance, 1-hexene-1,6-ylene, 2-hexene-1,6-ylene, 3-hexene-1,6-ylene, etc.), cyclopropenylene (for instance, 1-cyclopropene-1,2-ylene, 2-cyclopropene-1,2-ylene, etc.), cyclobutenylene (for instance, 1-cyclobutene-1,2-ylene, 1-cyclobutene-1,3-ylene, 2-cyclobutene-1,2-ylene, 3-cyclobutene-1,2-ylene, etc.), cyclopentenylene (for instance, 1-cyclopentene-1,2-ylene, 1-cyclopentene-1,3-ylene, 2-cyclopentene-1,2-ylene, 3-cyclopentene-1,2-ylene, 3-cyclopentene-1,3-ylene, 4-cyclopentene-1,3-ylene, etc.) or cyclohexenylene (for instance, 1-cyclohexene-1,2-ylene, 1-cyclohexene-1,3-ylene, 1-cyclohexene-1,4-ylene, 2-cyclohexene-1,2-ylene, 2-cyclohexene-1,4-ylene, 3-cyclohexene-1,2-ylene, 3-cyclohexene-1,3-ylene, 4-cyclohexene-1,2-ylene, 4-cyclohexene-1,3-ylene, etc.), alkynylene groups (for instance, ethynylene, propynylene, 1-butynylene, 2-butynylene, 1-pentynylene, 2-pentynylene, 3-pentynylene, etc.), cycloalkylene groups (for instance, 1,4-cyclohexylene, etc.), phenylene groups (for instance, o-phenylene, m-phenylene, p-phenylene, etc.), naphthylene groups or bivalent hydrocarbon groups obtained by replacing these hydrocarbon groups by materials as much as chemically permissible.

As the above-described cyclic compound, following compounds may be exemplified. They include, for example, a compound represented by a below-described formula,

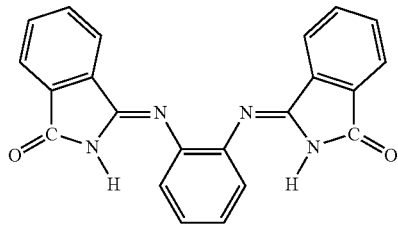

a compound represented by a below-described formula,

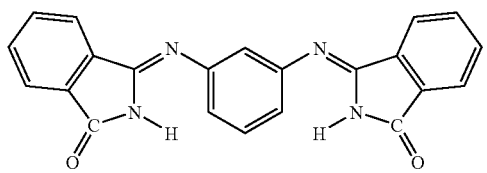

a compound represented by a below-described formula,

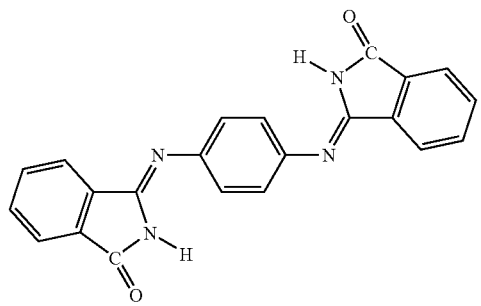

a compound represented by a below-described formula,

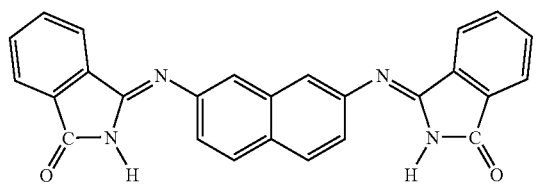

a compound represented by a below-described formula,

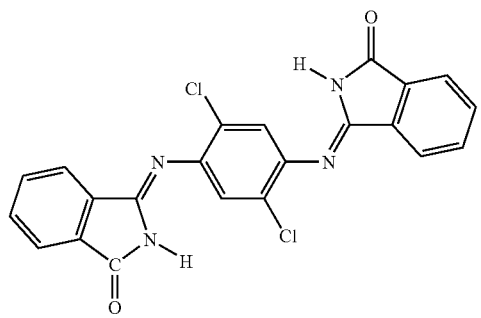

a compound represented by a below-described formula,

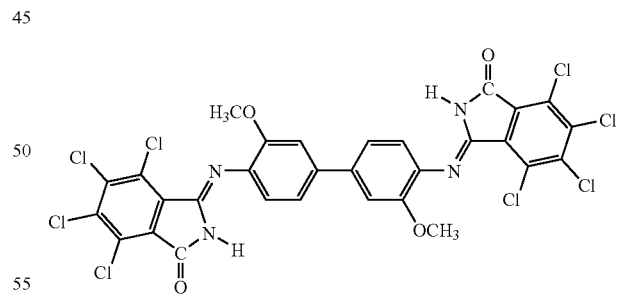

a compound represented by a below-described formula,

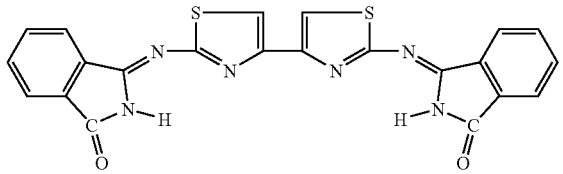

a compound represented by a below-described formula,

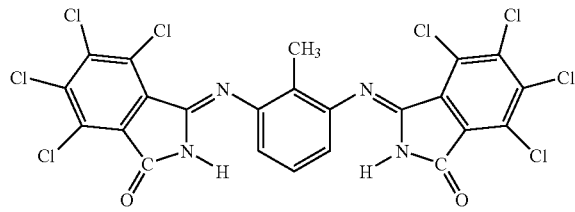

a compound represented by a below-described formula,

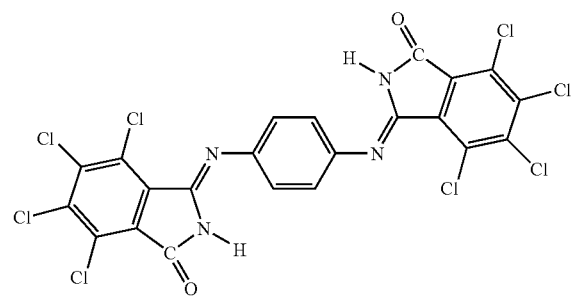

and a compound represented by a below-described formula,

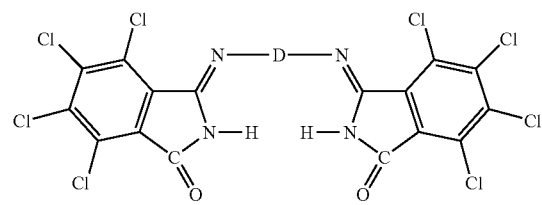

(In the formula, D shows a formula

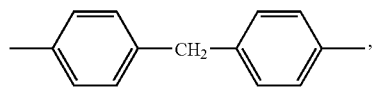

a formula

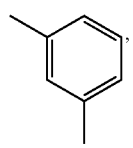

a formula

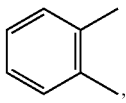

a formula

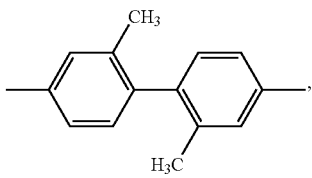

a formula

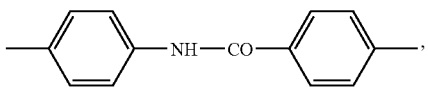

a formula

a formula

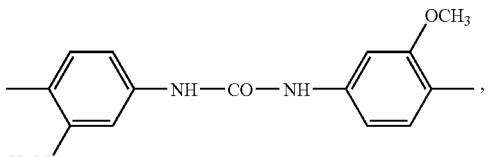

or a formula

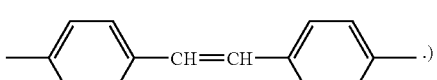

or compounds obtained by replacing these compounds by materials as much as possible chemically permissible. Further, these bivalent hydrocarbon groups may exemplify the bivalent hydrocarbon groups represented by B.

In the present invention, the cyclic compound is preferably 3,3'-(2-methyl-1,3-phenylene) diimino-bis-4,5,6,7-tetrachloro-1H-isoindole-1-one which is represented by a below-described formula.

This is frequently used as a yellow pigment (Pigment Yellow 109) that is conveniently available as marketed goods. The yellow pigment having various kinds of particle size is marketed. The pigment preferably has the particle size as small as possible. More specifically, the particle size of the particle is preferably about 10 µm or smaller, more preferably about 1 µm or smaller and most preferably about 0.1 µm or smaller.

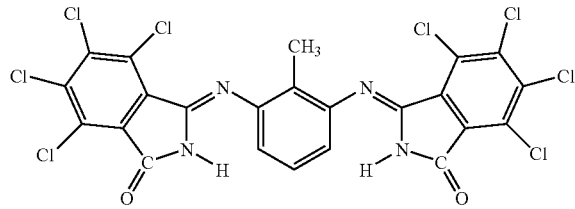

In the present invention, the cyclic compound is preferably 3,3'-(1,4-phenylene diimino) bis-4,5,6,7-tetrachloro-1H-isoindole-1-one which is represented by a below-described formula.

This is frequently used as a yellow pigment (Pigment Yellow 110) that is conveniently available as marketed goods. The yellow pigment having various kinds of particle size is marketed. The pigment preferably has the particle size as small as possible. More specifically, the particle size of the particle is preferably about 10 µm or smaller, more preferably about 1 µm or smaller and most preferably about 0.1 µm or smaller.

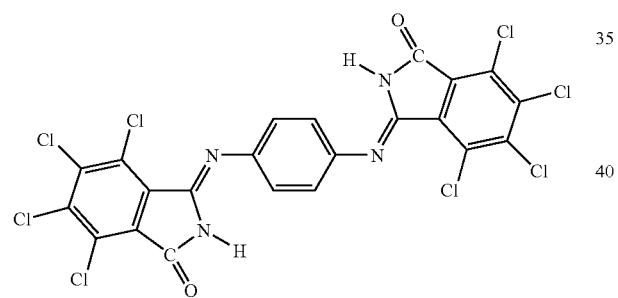

In the present invention, as the cyclic compound, an isomer of the above-described cyclic compound (for instance, a tautomer of the above-described cyclic compound, etc.) or the like can be employed.

Accordingly, a group represented by a below-described formula

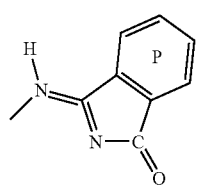

(in the formula, P shows the same meaning as described above) includes a group as its tautomer represented by a below-described formula

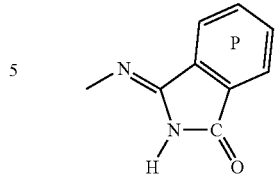

(in the formula, P shows the same meaning as described above). Further, according to the present invention, in the compound represented by the following formula,

A1-B-A2 one of A1 and A2 shows a group represented by a below-described formula (in the formula,

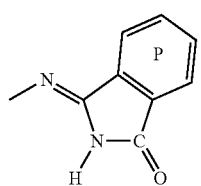

P shows the same meaning as described above) and the other includes a group represented by a below-described formula

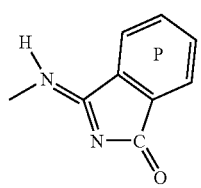

(in the formula, P shows the same meaning as described above).

Further, according to the present invention, in the compound represented by the following formula,

A1-B-A2 at least one of A1 and A2 includes a group represented by a below-described formula

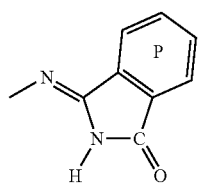

(P shows the same meaning as described above). More specifically, at least one of A1 and A2 includes, as an isomer of the cyclic compound, for example, a compound represented by a below-described formula,

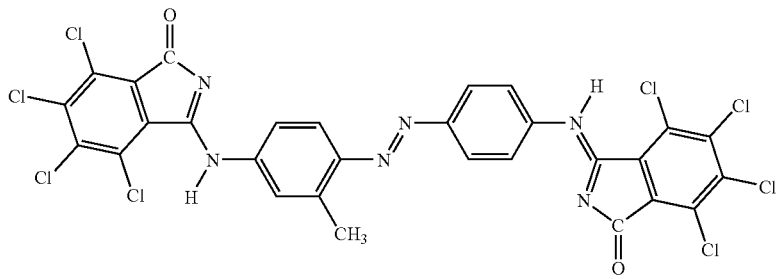

a compound represented by a below-described formula,

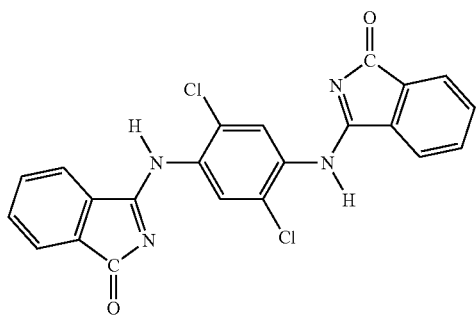

or a compound represented by a below-described formula.

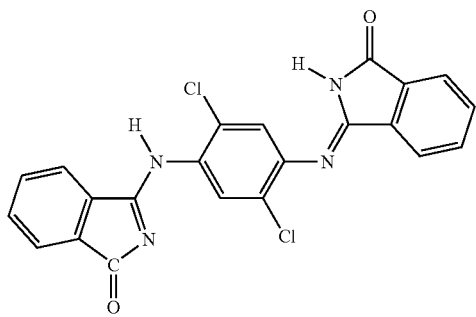

The cyclic compound used in the present invention preferably has the particle size as small as possible. More specifically, the particle size of the particle is preferably about 10 μm or smaller, more preferably about 1 μm or smaller and most preferably about 0.1 μm or smaller. In the present invention, the cyclic compound is preferably used as a nucleus agent for polyester capable of having a crystal structure.

The polyester capable of having the crystal structure is a polymer compound having at least one ester bond. Any of polyesters capable of having the crystal structures may be employed and well-known polyesters may be employed. Polyester "capable of having a crystal structure" may be polyester capable of partly having a crystal structure without a special limitation. In the polyester, all molecule chains cannot be necessarily regularly arranged. Even in case all the molecule chains do not have regularity in the polyester, when at least two molecule chain segments can be oriented, any polyester may be used. Accordingly, the polyester capable of having the crystal structure preferably has straight chains, however, may have branches. Further, in the present invention, the polyester capable of having the crystal structure is preferably biodegradable polyester. As such biodegradable polyesters, for example, polyesters subjected to a metabolic action by microorganisms may be exemplified. Aliphatic polyester having a moldability, a heat resistance and a shock resistance with good balance is preferably used among them.

As the aliphatic polyesters, for example, polyoxalic acid, polysuccinic acid, polyhydroxy butyric acid, butylene polydiglycolic acid, polycaprolactone, polydioxanone, polylactic acid based aliphatic polyester, etc. may be exemplified. As the aliphatic polyester, the polylactic acid based aliphatic polyester is more preferably used among them. As the polylactic acid based aliphatic polyester, polymers of hydroxy acid such as lactic acid, malic acid, glycolic acid, etc. or copolymers of them may be specifically exemplified. Hydroxy carboxylic acid based aliphatic polyester that typically includes polylactic acid is especially preferably used among them. Further, polylactic acid is most preferable among the hydroxy carboxylic acid based aliphatic polyesters.

The biodegradable polyester used in the present invention can be produced in accordance with a known method. For example, the biodegradable polyester can be produced by methods such as a lactide method, a polycondensation of polyhydric alcohol and polybasic acid, or an intermolecular polycondensation of hydroxy carboxylic acid having a hydroxyl group and a carboxyl group in molecules.

Particularly, the polylactic acid based aliphatic polyester can be ordinarily obtained by a method in accordance with a ring-opening polymerization of lactide as cyclic diester and corresponding lactones, what is called a lactide method, or a direct dehydration condensation method of lactic acid except the lactide method. Further, as a catalyst for producing the polylactic acid based aliphatic polyester, tin, antimony, zinc, titanium, iron, aluminum compounds, etc. may be exemplified. Tin catalyst and aluminum catalyst are preferably used among them and tin octylate and aluminum acetylacetonate are more preferably employed.

Poly L-lactic acid obtained by the lactide ring-opening polymerization is most preferable among the polylactic acid based aliphatic polyesters. The poly L-lactic acid is hydrolyzed to have L-lactic acid and its safety is recognized. The polylactic acid based aliphatic polyester employed in the present invention is not limited thereto. Accordingly, the lactide used for producing the polylactic acid based aliphatic polyester is not also limited to L forms. Further, in the present invention, as the biodegradable polyester, a marketed product such as the name of a product H100J (produced by Mitsui Chemicals, Inc.) may be used.

In the resin component according to the present invention, polyester having not necessarily crystal structure or other biodegradable resins may be further included as resin constituents. As such biodegradable resins, below-described materials may be exemplified and there are many kinds of materials that can be employed in the present invention. They include, for example, polysaccharide derivatives such as cellulose, starch, dextran, chitin, etc., peptides such as collagen, casein, fibrin, gelatin, etc., polyamides such as polyamino acid, polyvinyl alcohol, nylon 4 or nylon 2/nylon 6 copolymers, etc., polyesters such as polyglycolic acid, polylactic acid, polysuccinic acid esters, polyoxalic acid esters, polyhydroxy butyric acid, butylene polydiglycolic acid, polycaprolactone, polydioxanone, etc. which have been known as materials having no crystal structure. That is, biodegradable polymers are organic materials decomposed and assimilated by the actions of the natural world and vital materials and any of ideal materials adapted to an environment that do not injure the objects of the present invention may be employed.

The biodegradable resin used in the present invention can be produced in accordance with the known methods. Further, as the biodegradable resin, a marketed product may be used. For example, Lacty (produced by Shimadzu Corporation), Lacea (produced by Mitsui Chemicals, Inc.) or Nature Works (produced by Cargill Dow Polymers LLC) etc. may be exemplified.

In the resin component according to the present invention, one kind of the above-described biodegradable resins may be included and two or more kinds of the biodegradable resins may be included. When the two or more kinds of biodegradable resins are included, these resins may form copolymers or may be mixed together.

In the resin component according to the present invention, resins except the above-described biodegradable resins may be included. For example, synthetic resins having no biodegradable property or the like may be included. As the above-described resins, for example, polylactic acid, polybutylene succinate, etc. which moderates decomposition speed may be exemplified.

To the resin component according to the present invention, inorganic filler may be added. As the inorganic filler, well-known fillers may be used. For example, talc, alumina, silica, magnesia, mica, kaolin, etc. may be exemplified. Since talc among them is used together with the cyclic compound employed in the present invention to effectively accelerate the crystallization without canceling their effects with each other, talc is more preferably employed.

The inorganic filler of about 1 to 50 parts by weight is preferably added relative to polyester capable of having a crystal structure of 100 parts by weight. When the amount of the inorganic filler is located within the above-described range, the obtained resin component can be avoided from being brittle.

The suppression of hydrolysis of polyester is important in view of reliability for a long period in use of the moldings. Accordingly, a hydrolysis inhibitor is further preferably added to the resin component according to the present invention. As such a hydrolysis inhibitor, any of hydrolysis inhibitors that can suppress the hydrolysis of the biodegradable resin may be used without special limitation. For example, compounds having reactivity with active hydrogen in the biodegradable resin may be exemplified. The above-described compound is added to the biodegradable resin to reduce the amount of active hydrogen in the biodegradable resin, so that the active hydrogen can be prevented from hydrolyzing polymer chains forming the biodegradable resin like a catalyst. Here, the active hydrogen indicates hydrogen in the bond of oxygen, nitrogen, etc. with hydrogen (N—H bond or O—H bond). This hydrogen has reactivity higher than that of hydrogen in the bond of carbon and hydrogen (C—H bond). More specifically, hydrogen in a carboxyl group: —COOH, hydroxyl group: —OH, an amino group: —NH2, an amide bond: —NHCO— etc. in the biodegradable resin may be exemplified.

As the hydrolysis inhibitor, for example, carbodiimide compounds, isocyanate compounds or oxazoline compounds may be applied thereto. Especially, since the carbodiimide compound can be melted and kneaded with a biodegradable polymer compound and can more suppress the hydrolysis of the biodegradable resin with a small amount of addition, the carbodiimide compound is preferable.

The carbodiimide compound is a compound having one or more carbodiimide groups in a molecule and includes a polycarbodiimide compound. As monocarbodiimide compounds included in the carbodiimide compounds, dicyclohexyl carbodiimide, diisopropyl carbodiimide, dimethyl carbodiimide, diisobutyl carbodiimide, dioctyl carbodiimide, diphenyl carbodiimide, naphthyl carbodiimide, etc. may be exemplified. Dicyclohexyl carbodiimide or diisopropyl carbodiimide that is especially industrially available is preferable among them.

As the isocyanate compounds, for example, 2,4-tolylene diisocyanate, 2,6-tolylene diisocyanate, m-phenylene diisocyanate, p-phenylene diisocyanate, 4,4'-diphenyl methane diisocyanate, 2,4'-diphenyl methane diisocyanate, 2,2'-diphenyl methane diisocyanate, 3,3'-dimethyl-4,4'-biphenylene diisocyanate, 3,3'-dimethoxy-4,4'-biphenylene diisocyanate, 3,3'-dichloro-4,4'-biphenylene diisocyanate, 1,5-naphthalene diisocyanate, 1,5-tetrahydro naphthalene diisocyanate, tetramethylene diisocyanate, 1,6-hexamethylene diisocyanate, dodecamethylene diisocyanate, trimethyl hexamethylene diisocyanate, 1,3-cyclohexylene diisocyanate, 1,4-cyclohexylene diisocyanate, xylylene diisocyanate, tetramethyl xylylene diisocyanate, hydrogenated xylylene diisocyanate, lysine diisocyanate, isophorone diisocyanate, 4,4'-dicyclohexyl methane diisocyanate, 3,3'-dimethyl-4,4'-dicyclohexyl methane diisocyanate, etc. may be exemplified.

As the oxazoline compounds, for example, 2,2'-o-phenylene bis (2-oxazoline), 2,2'-m-phenylene bis(2-oxazoline), 2,2'-p-phenylene bis (2-oxazoline), 2,2'-p-phenylene bis(4-methyl-2-oxazoline), 2,2'-m-phenylene bis (4-methyl-2-oxazoline), 2,2'-p-phenylene bis(4,4'-dimethyl-2-oxazoline), 2,2'-m-phenylene bis(4,4'-dimethyl-2-oxazoline), 2,2'-ethylene bis(2-oxazoline), 2,2'-tetramethylene bis(2-oxazoline), 2,2'-hexamethylene bis(2-oxazoline), 2,2'-octamethylene bis (2-oxazoline), 2,2'-ethylene bis(4-methyl-2-oxazoline), 2,2'-diphenylene bis(2-oxazoline), etc. may be exemplified.

The above-described hydrolysis inhibitors can be easily produced in accordance with well-known methods and marketed products may be suitably employed.

Since the biodegradation speed of the resin component of the present invention can be adjusted depending on the kinds or the amount of addition of the hydrolysis inhibitor used in the present invention, the kind and a quantity of mixing of the hydrolysis inhibitor to be mixed may be determined in accordance with a desired product. The amount of addition of the hydrolysis inhibitor is not especially limited to a specific value, however, the amount of addition of the hydrolysis inhibitor is ordinarily 5 wt % or lower relative to all the weight of the resin component and preferably 1 wt %. Further, as the hydrolysis inhibitor, the above-described compounds may be independently used or two or more kinds of compounds may be used together.

To the resin component according to the present invention, various kinds of conventionally well-known addition agents such as an antioxidant, an optical stabilizer, an ultraviolet absorbent, pigment, a colorant, an antistatic agent, a mold releasing agent, perfume, lubricant, a flame retardant, a filler, an antibacterial or antifungal agent, etc. may be added as desired so as not to seriously interfere with a crystallization or a crystalline property.

The resin component according to the present invention is produced in such a way that the above-described cyclic compounds or the mixture thereof, polyester capable of having the crystal structure and further other constituents are mixed together as desired. As a specific method for producing the resin component according to the present invention from the respective constituents as raw materials thereof, a method that the biodegradable resin as a raw material is mixed with the inorganic filler, the hydrolysis inhibitor or the like as desired and the mixture was melted and kneaded by using an extruder is exemplified. As a method for producing the resin component as well as the above-described method, what is called a solution method may be employed. Here, the solution method is a method that arbitrary solution capable of dispersing and dissolving the respective constituents is used to completely agitate the constituents as raw materials and solvent, form slurry and dry and removed the solvent.

The method for producing the resin component according to the present invention is not limited to these methods and conventionally well-known methods except these methods may be employed.

In the present invention, the cyclic compound is preferably uniformly and finely dispersed in the biodegradable polyester. A conventionally well-known method may be employed for this purpose. For example, a method for dispersing pigment in the resin and coloring the resin may be used. For example, a method that three rolls are used may be exemplified. Otherwise, a method that the cyclic compound is mixed with polyester, and then, the mixture is repeatedly heated and kneaded a plurality of times is exemplified. Specifically, for example, a method that the mixture of the cyclic compound and the polyester is supplied to a known melting and mixing machine such as a uniaxial or biaxial extruder, a Banbury mixer, a kneader, a mixing roll, etc. and kneaded at the temperature of about 170 to 380° C. may be exemplified. Further, when the addition agent is added to the mixture, after the mixture is kneaded by the above-described method and pelletized, the addition agent may be added thereto before molding.

In the present invention, the mixing ratio of the cyclic compound in the resin component is preferably located within a range of about 0.001 to 10 parts by weight relative to the polyester capable of having the crystal structure of 100 parts by weight, and more preferably located within a range of about 0.01 to 1 parts by weight. Further, in the present invention, the crystallization rate of the resin component is preferably located within a range of about 20 to 100%, and more preferably located within a range of about 40 to 100%. Further, the crystallization time of the resin component is preferably located within a range of about 0 to 1000 seconds, and more preferably located within a range of about 0 to 200 seconds. The modulus of elasticity of the resin component at 80° C. is preferably located within a range of about 10 to 10000 MPa and the modulus of elasticity of the resin component at 80° C. is more preferably located within a range of about 50 to 5000 MPa. The crystallization rate and the crystallization time are respectively obtained by referring to below-described Examples. The modulus of elasticity is obtained by a measuring method including a tensile elasticity measurement and a bending elasticity measurement.

| | |
|---|---|
| Specimen: | length of 50 mm × width of 7 mm × thickness of 1 mm |
| Measuring device: | viscoelastic analyzer RSA-II (produced by Rheometric) |
| Measuring geometry: | Dual Cantilever Bending |
| Frequency: | 6.28 (rad/s) |
| Measurement start temperature: | 0 (° C.) |
| Measurement end temperature: | 160 (° C.) |
| Temperature rise speed: | 5 (° C./min) |
| Distortion: | 0.05 (%) |

The resin component according to the present invention can be widely used for various kinds of moldings. Since the crystalline property of the resin component is high, the moldings made of the resin component according to the present invention are excellent in their rigidity and the transparency thereof can be improved. Thus, the moldings can be preferably used as products that highly require such a rigidity and transparency. As the uses of the moldings using the resin component according to the present invention, such products as described below may be exemplified. They include, for example, a power generator, an electric motor, a transformer, a current transformer, a voltage regulator, a rectifier, an inverter, a relay, a contact for power, a switch, a machine circuit breaker, a knife switch, a rod for other electrode, an electric machine parts cabinet, a light socket, various kinds of terminal boards, electric device parts such as a plug or a power module, a sensor, an LED lamp, a connector, a resistor, a relay case, a small switch, a coil bobbin, a capacitor, a variable condenser case, an optical pick-up, an oscillator, a transformer, a printed circuit board, a tuner, a speaker, a microphone, a headphone, a storage device such as a floppy (registered trade mark) disc or an MO disc, a small motor, a magnetic head base, a semiconductor, a liquid crystal, an FDD carriage, an FDD chassis, a printer such as an ink jet printer or a thermal transfer printer, a motor brush holder, electronic parts such as a parabolic antenna or parts related to a computer, VTR parts, television parts, a casing of an electric or electronic device such as a television or a personal computer, home and office electric product parts including an iron, a hair drier, rice boiler parts, microwave oven parts, acoustic device parts such as an acoustic product or an audio laser disc (registered trade mark) and compact disc, lighting parts, refrigerator parts, air conditioner parts, typewriter parts or word processor parts, parts related to machines such as parts related to an office computer, parts related to a telephone, parts related to facsimile device parts, parts related to a copying machine, a cleaning jig, motor parts and a writer or a typewriter, parts related to optical devices and precision machine such as a microscope, a binocular telescope, a camera, a clock, etc., parts related to a motor vehicle or a vehicle such as an alternator terminal, an alternator connector, an IC regulator, a potentiometer base for a light dayer or various valves such as exhaust gas valves, various kinds of pipes for fuel systems, exhaust and intake systems, an air intake nozzle snorkel, an intake manifold, a fuel pump, an engine cooling water joint, a carburetor main body, a carburetor spacer, an exhaust gas sensor, a cooling water sensor, an oil temperature sensor, a brake pad wear sensor, a throttle position sensor, a crankshaft position sensor, an air flow meter, a brake pad abrasion sensor, a thermostat base for an air conditioner, an air flow control valve for heating, a brush holder for a radiator motor, a water pump impeller, a turbine vane, parts related to a wiper motor, a distributor, a starting switch, a starter relay, a wire harness for a transmission, a window washer nozzle, an air conditioner panel switch board, a coil for an electromagnetic valve related to fuel, a connector for a fuse, a horn terminal, an insulating plate for an electrical parts, a stepping motor roller, a lamp socket, a lamp reflector, a lamp housing, a brake piston, a solenoid bobbin, an engine oil filter or an ignition device case, package materials, etc. The moldings are preferably employed among them as the casings of electric or electronic devices such as televisions or personal computers that are mass-produced. After these products are used, they may be subjected to a biodegradation process and disposed. An excessive energy is not advantageously consumed for disposal of the products.

Now, another embodiment of a resin component according to the present invention will be described below.

The resin component according to the present invention comprises one or more cyclic compounds selected from between a copper phthalocyanine crystal (a) which may be replaced by a material, a phthalocyanine compound (b) which may include one kind of metal selected from between zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium which may be replaced by a material and a porphyrin compound (c) which may be replaced by a material, and polyester capable of having the crystal structure.

In the resin component according to the present invention, a compound which may be replaced by a material means a compound in which substituent groups may be included. As the "substituent groups", such substituent groups as described below may be exemplified. They include, for instance, halogen atoms (for instance, fluorine, chlorine, bromine, iodine, etc.), nitro groups, cyano groups, hydroxy groups, thiol groups, sulfo groups, sulfino groups, mercapto groups, phosphono groups, alkyl groups (for instance, methyl groups, ethyl groups, isopropyl groups, n-propyl groups, n-butyl groups, isobutyl groups, secondary butyl groups, tertiary butyl groups or various kinds of other isomers such as pentyl groups, hexyl groups, heptyl groups, octyl groups, nonyl groups, decyl groups, undecyl groups, dodecyl groups, tridecyl groups, tetradecyl groups, pentadecyl groups, hexadecyl groups, heptadecyl groups, octadecyl groups, nonadecyl groups, eicosyl groups, etc.), hydroxy alkyl groups (for instance, hydroxy methyl groups, hydroxy ethyl groups, 1-hydroxy isopropyl groups, 1-hydroxy-n-propyl groups, 2-hydroxy-n-butyl groups, 1-hydroxy-isobutyl groups, 1-hydroxy-secondary butyl groups, 1-hydroxy-tertiary butyl groups, etc.), halogeno alkyl groups (for instance, chloromethyl, dichloromethyl, trichloromethyl, fluoromethyl, difluoromethyl, trifluoromethyl, 2-bromoethyl, 2,2,2-trifluoroethyl, pentafluoro ethyl, 3,3,3-trifluoro propyl, 4,4,4-trifluoro butyl, 5,5,5-trifluoro pentyl, 6,6,6-trifluoro hexyl, etc.), cycloalkyl groups (for instance, cyclopropyl, cyclobutyl, cyclopentyl, cyclohexyl, cycloheptyl, etc.), alkenyl groups (for instance, vinyl, crotyl, 2-pentenyl, 3-hexenyl, etc.), cycloalkenyl groups (for instance, 2-cyclopentenyl, 2-cyclohexenyl, 2-cyclopentenyl methyl, cyclohexenyl methyl, etc.), alkynyl groups (for instance, ethynyl, 1-propynyl, 2-propynyl, 1-butynyl, 2-pentynyl, 3-hexynyl, etc.), oxo groups, thioxo groups, amidino groups, imino groups, alkylenedioxy groups (for instance, methylenedioxy, ethylenedioxy, etc.), hydrocarbon groups including, for example, monocyclic or polycyclic hydrocarbon groups such as phenyl, biphenyl, etc., or cross-linked hydrocarbon groups such as 1-adamantyl groups, 2-norbornanyl, etc., alkoxy groups (for instance, methoxy, ethoxy, propoxy, isopropoxy, butoxy, isobutoxy, sec-butoxy, tert-butoxy, pentyloxy, neopentyloxy, hexyloxy, etc.), alkylthio groups (for instance, methylthio, ethylthio, propylthio, isopropylthio, butylthio, isobutylthio, pentylthio, hexylthio, etc.), carboxyl groups, alkanoyl groups (for instance, formyl; acetyl, propionyl, butyryl, isobutyryl, etc.), alkanoyloxy groups (for instance, formyloxy; alkyl-carbonyloxy groups such as acetyloxy, propionyloxy, butyryloxy, isobutyryloxy, etc.), alkoxy carbonyl groups (for instance, methoxy carbonyl, ethoxy carbonyl, propoxy carbonyl, butoxy carbonyl, etc.), aralkyloxy carbonyl groups (for instance, benzyloxy carbonyl, etc.), thiocarbamoyl groups, alkyl sulfinyl groups (for instance, methyl sulfinyl, ethyl sulfinyl, etc.), alkyl sulfonyl groups (for instance, methyl sulfonyl, ethyl sulfonyl, butyl sulfonyl, etc), sulfamoyl groups, mono-alkyl sulfamoyl groups (for instance, methyl sulfamoyl, ethyl sulfamoyl, etc.), di-alkyl sulfamoyl groups (for instance, dimethyl sulfamoyl, diethyl sulfamoyl, etc.), allyl sulfamoyl groups (for instance, phenyl sulfamoyl, naphthyl sulfamoyl, etc.), allyl groups (for instance, phenyl, naphthyl, etc.), allyloxy groups (for instance, phenyloxy, naphthyloxy, etc.), allylthio groups (for instance, phenylthio, naphthylthio, etc.), allyl sulfinyl groups (for instance, phenyl sulfinyl, naphthyl sulfinyl, etc.), allyl sulfonyl groups (for instance, phenyl sulfonyl, naphthyl sulfonyl, etc.), allyl carbonyl groups (for instance, benzoyl, naphthoyl, etc.), allyl carbonyloxy groups (for instance, benzoyloxy, naphthoyloxy, etc.), alkyl carbonyl amino groups which may be halogenated (for instance, acetyl amino, trifluoro acetyl amino, etc.), carbamoyl groups which may have substituent groups (for instance, groups represented by a formula —CONR3R4 (in the formula, R3 and R4 respectively show hydrogen atoms, hydrocarbon groups which may have substituent groups or heterocyclic groups which may have substituent groups, or R3 and R4 may form a ring with an adjacent nitrogen atom.)), amino groups which may have substituent groups (for instance, amino, alkyl amino, tetrahydro pyrrole, piperazine, piperidine, morpholine, thiomorpholine, pyrrole, imidazole, etc.), ureido groups which may have substituent groups (for instance, groups represented by a formula —NHCONR3R4 (in the formula, R3 and R4 show the same meanings as described above) or the like)), carboxamide groups which may have substituent groups (for instance, groups represented by a formula —NR3COR4 (in the formula, R3 and R4 show the same meanings as described above)), sulfonamide groups which may have substituent groups (for instance, groups represented by a formula —NR3SO2R4 (in the formula, R3 and R4 show the same meanings as described above), etc.), hydroxyl groups or mercapto groups which may have substituent groups, heterocyclic groups which may have substituent groups (for instance, aromatic heterocyclic groups (for instance, pyridyl, furyl, thiazolyl, etc.) including at least one of one to three kinds of hetero atoms selected from oxygen atoms, sulfur atoms and nitrogen atoms as well as carbon atoms as atoms (annular atoms) forming a cyclic system, or saturated or unsaturated aliphatic heterocyclic groups, etc., saturated or unsaturated aliphatic heterocyclic groups, etc.) or substituent groups obtained by replacing these substituent groups by materials as much as chemically permissible.

Now, preferred embodiments of constituents will be respectively described below.

As the above-described copper phthalocyanine crystal described in (a), any of crystals of phthalocyanine compounds including copper may be used without special limitation in the present invention. Well-known materials called copper phthalocyanine crystals may be employed. For example, a crystal of a compound represented by a below-described formula is exemplified.

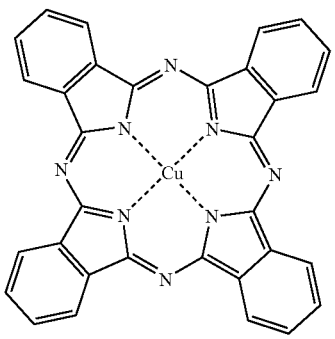

In the present invention, the crystal of a copper phthalocyanine substituent by which the above-described compound is replaced as much as chemically permissible may be also used as the copper phthalocyanine crystal. For example, halogenated copper phthalocyanine or the like may be exemplified. As the halogenated copper phthalocyanine, a material obtained by replacing hydrogen of a benzene ring of copper phthalocyanine by chlorine is exemplified. Further, halogen may be bromine, fluorine or iodine. As substituent groups except halogens, for instance, alkyl groups such as methyl, ethyl, etc., alkoxy groups such as methoxy, ethoxy, etc., hydroxyl groups, amino groups, etc. may be exemplified.

As the above-described phthalocyanine compound shown in (b) which may include one kind of metal selected from between zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium which may be replaced by a material, any of compounds including phthalocyanine groups having no metal or compounds including phthalocyanine groups having one kind of metal selected from between zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium may be employed and the compound is not especially limited to a specific compound in the present invention. As the "compounds including phthalocyanine groups having no metal", for example, metal free phthalocyanine represented by a below-described formula and having no metal at a center is exemplified.

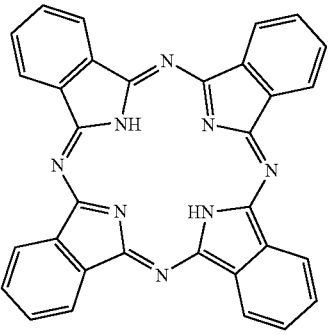

As the "compounds including phthalocyanine groups having one kind of metal selected from between zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium", for example, a phthalocyanine compound represented by a below-described formula

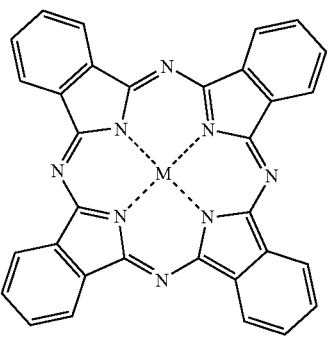

(in the formula, M designates one kind of metal selected from between zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium.) and having metal at a center may be exemplified.

In the present invention, as the phthalocyanine compounds, well-known compounds referred to as phthalocyanine compounds may be employed. For example, metal free phthalocyanine, titanyl phthalocyanine, aluminum phthalocyanine, vanadium phthalocyanine, cadmium phthalocyanine, antimony phthalocyanine, chromium phthalocyanine, germanium phthalocyanine, iron phthalocyanine, chloroaluminum phthalocyanine, chloroindium phthalocyanine, chlorogallium phthalocyanine, magnesium phthalocyanine, dialkyl phthalocyanine, tetramethyl phthalocyanine, tetraphenyl phthalocyanine, etc. may be employed. In the present invention, for example, marketed products having the products names of metal free phthalocyanine, aluminum phthalocyanine, titanyl phthalocyanine, iron phthalocyanine, cobalt phthalocyanine, tin phthalocyanine (produced by Sanyo Color Works, Ltd,) may be employed. Further, in the present invention, an uranium complex (super phthalocyanine) having five isoindole rings or a boron complex having three isoindole rings can be also used as the phthalocyanine compounds. Phthalocyanine substituents by which the phthalocyanine compounds are replaced as much as chemically permissible can be also preferably used as the phthalocyanine compounds. For example, halogenated phthalocyanine or the like is frequently used as a green pigment and a marketed product can be used. Halogen may be chlorine, bromine, fluorine, iodine, etc. As the substituent groups except the halogen, for example, alkyl groups such as methyl, ethyl, etc., alkoxy groups such as methoxy, ethoxy, etc, hydroxyl groups, amino groups, etc. may be exemplified.

Most of copper phthalocyanine and phthalocyanine compounds are capable of forming crystals by a regular molecular arrangement. They may have some crystal forms depending on forming conditions. For example, in the copper phthalocyanine, molecules may be arranged in one direction so as to stack cards and rows may form bundles to form crystals. The ways of stacks (inclination angles of planes of molecules relative to an axis and distances between molecules) and the ways of arrangements of rows are different so that many kinds of crystals may be formed. The copper phthalocyanine crystal may take crystal forms such as an alpha type, a beta type, a gamma type, a delta type, a sigma type, an epsilon type, a pie type, a rho type, a tau type, a xi type or an R type. In the present invention, the copper phthalocyanine crystal preferably has a crystal called the beta type or the epsilon type from the reason why the capability of the nucleus agent of crystalline polyester is high. The above-described copper phthalocyanine crystal is frequently used as a blue pigment and the copper phthalocyanine crystals of various crystal types are available from marketed products.

As the above-described porphyrin compound which may be replaced by a material shown in (c), any of compounds including porphyrin groups may be employed without a special limitation in the present invention. Further, compounds called porphyrin compounds may be employed. For example, a compound represented by a below-described compound,

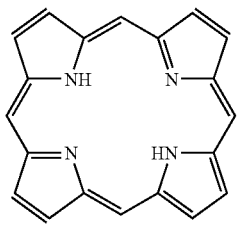

a chlorophyll compound represented by a below-described formula

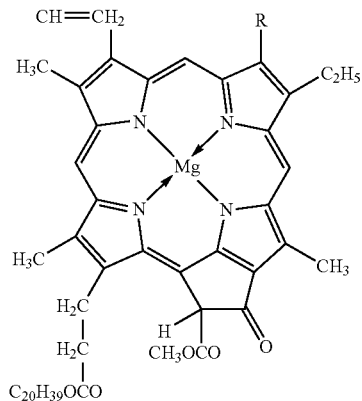

(in the formula, R designates hydrocarbon groups, halogen, etc. which may be replaced by a material.), or a haemin compound represented by a below-described formula

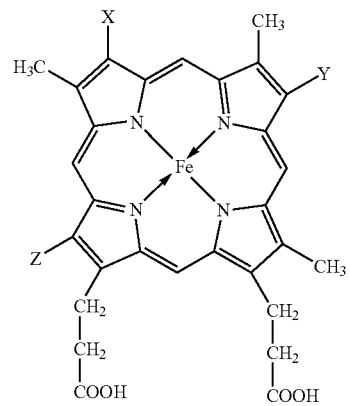

(in the formula, X, Y and Z are the same or different and show hydrocarbon groups, hydrogens, etc. which may be replaced by materials.), or esters in carboxyl groups thereof may be exemplified.

As the "hydrocarbon groups which may be replaced by materials", any of the hydrocarbon groups which are replaced by one or more of the above-described substituent groups or hydrocarbon groups which are not replaced by materials may be employed without a special limitation. As the "hydrocarbon groups", for instance, alkyl groups, alkenyl groups, alkynyl groups, cycloalkyl groups, allyl groups, cross-linked hydrocarbon groups, etc. may be exemplified. As the "alkyl groups", straight chain type or branch type alkyl groups (for example, methyl, ethyl, n-propyl, isopropyl, n-butyl, isobutyl, sec-butyl, tert-butyl, n-pentyl, isoamyl, tert-amyl, n-hexyl, isohexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-eicosyl, n-docosyl, n-tetracosyl etc.) may be exemplified. As the "alkenyl groups", for example, straight chain type or branch type alkenyl groups such as vinyl, propenyl (1-, 2-), butenyl (1-, 2-, 3-), pentenyl, octenyl, butadienyl (1,3-) etc. may be exemplified. As the "alkynyl groups", for example, straight chain type or branch type alkynyl groups such as ethynyl, propynyl (1-, 2-), butynyl (1-, 2-, 3-), pentynyl, octynyl, decynyl, etc. may be exemplified. As the "cycloalkyl groups", for example, cyclopropyl, cyclobutyl, cyclopentyl, cyclohexyl, cycloheptyl, cyclooctyl, etc. may be exemplified. As the "allyl groups", for example, monocyclic or polycyclic groups such as phenyl, biphenyl, naphthyl, anthryl, phenanthryl, acenaphthylenyl, etc. may be exemplified. As the "cross-linked hydrocarbon groups", for example, 1-adamantyl, 2-adamantyl, 2-norbornanyl, 5-norbornene-2-yl, etc. may be exemplified. To these cyclic compounds, substituent groups may be introduced within a chemically permissible range. The cyclic compounds may be, for example, halogenated materials or sulfonated materials.

In the present invention, the above-described cyclic compound preferably has a particle size of about 100 μm or smaller and more preferably has the particle size of the particle of about 10 μm or smaller. Further, in the present invention, the cyclic compound is also commercially valuable as a nucleus agent for polyester capable of having a crystal structure. In that case, the cyclic compound may be diluted by a diluting agent of suitable solvent.

The polyester capable of having the crystal structure is a polymer compound having at least one ester bond. Any of polyesters capable of having the crystal structures may be employed and well-known polyesters may be employed. Polyester "capable of having a crystal structure" may be polyester capable of partly having a crystal structure without a special limitation. In the polyester, all molecule chains cannot be necessarily regularly arranged. Even in case all the molecule chains do not have regularity in the polyester, when at least two molecule chain segments can be oriented, any polyester may be used. Accordingly, the polyester capable of having the crystal structure preferably has straight chains, however, may have branches. Further, in the present invention, the polyester capable of having the crystal structure is preferably biodegradable polyester. As such biodegradable polyesters, for example, polyesters subjected to a metabolic action by microorganisms may be exemplified. Aliphatic polyester having a moldability, a heat resistance and a shock resistance with good balance is preferably used among them.

As the aliphatic polyesters, for example, polyoxalic acid, polysuccinic acid, polyhydroxy butyric acid, polydiglycolic acid, polycaprolactone, polydioxanone, polylactic acid based aliphatic polyester, etc. may be exemplified. As the aliphatic polyester, the polylactic acid based aliphatic polyester is more preferably used among them. As the polylactic acid based aliphatic polyester, polymers of hydroxy acid such as lactic acid, malic acid, glycolic acid, etc. or copolymers of them may be specifically exemplified. Hydroxy carboxylic acid based aliphatic polyester that typically includes polylactic acid is especially preferably used among them. Further, polylactic acid is most preferable among the hydroxy carboxylic acid based aliphatic polyesters.

The biodegradable polyester used in the present invention can be produced in accordance with a known method. For example, the biodegradable polyester can be produced by methods such as a lactide method, a polycondensation of polyhydric alcohol and polybasic acid, or an intermolecular polycondensation of hydroxy carboxylic acid having a hydroxyl group and a carboxyl group in molecules.

Particularly, the polylactic acid based aliphatic polyester can be ordinarily obtained by a method in accordance with a ring-opening polymerization of lactide as cyclic diester and corresponding lactones, what is called a lactide method, or a direct dehydration condensation method of lactic acid except the lactide method. Further, as a catalyst for producing the polylactic acid based aliphatic polyester, tin, antimony, zinc, titanium, iron, aluminum compounds, etc. may be exemplified. Tin catalyst and aluminum catalyst are preferably used among them and tin octylate and aluminum acetylacetonate are more preferably employed.

Poly L-lactic acid obtained by the lactide ring-opening polymerization is most preferable among the polylactic acid based aliphatic polyesters. The poly L-lactic acid is hydrolyzed to have L-lactic acid and its safety is recognized. The polylactic acid based aliphatic polyester employed in the present invention is not limited thereto. Accordingly, the lactide used for producing the polylactic acid based aliphatic polyester is not also limited to L forms. Further, in the present invention, as the biodegradable polyester, a marketed product such as the name of a product H100J (produced by Mitsui Chemicals, Inc.) may be used.

In the resin component according to the present invention, polyester that does not necessarily have a crystal structure or other biodegradable resins may be further included as resin constituents. As such biodegradable resins, below-described materials may be exemplified and there are many kinds of materials that can be employed in the present invention. They include, for example, polysaccharide derivatives such as cellulose, starch, dextran, chitin, etc., peptides such as collagen, casein, fibrin, gelatin, etc., polyamides such as polyamino acid, polyvinyl alcohol, nylon 4 or nylon 2/nylon 6 copolymers, etc., polyesters such as polyglycolic acid, polylactic acid, polysuccinic acid esters, polyoxalic acid esters, polyhydroxy butyric acid, butylene polydiglycolic, polycaprolactone, polydioxanone, etc. which have been known as materials having necessarily no crystal structure. That is, biodegradable polymers are organic materials decomposed and assimilated by the actions of the natural world and vital materials and any of ideal materials adapted to an environment that do not injure the objects of the present invention may be employed.

The biodegradable resin used in the present invention can be produced in accordance with the known methods. Further, as the biodegradable resin, a marketed product may be used. For example, Lacty (produced by Shimadzu Corporation), Lacea (produced by Mitsui Chemicals, Inc.) or Nature Works (produced by Cargill Dow Polymers LLC) etc. may be exemplified.

In the resin component according to the present invention, one kind of the above-described biodegradable resins may be included and two or more kinds of the biodegradable resins may be included. When the two or more kinds of biodegradable resins are included, these resins may form copolymers or may be mixed together.

In the resin component according to the present invention, resins except the above-described biodegradable resins may be included. For example, synthetic resins having no biodegradable property or the like may be included. As the above-described resins, for example, polylactic acid, polybutylene succinate, etc. which moderates decomposition speed may be exemplified.

To the resin component according to the present invention, inorganic filler may be added. As the inorganic filler, well-known fillers may be used. For example, talc, alumina, silica, magnesia, mica, kaolin, etc. may be exemplified. Since talc among them is used together with the cyclic compound employed in the present invention to effectively accelerate the crystallization without canceling their effects with each other, talc is more preferably employed.

The inorganic filler of about 1 to 50 parts by weight is preferably added relative to polyester capable of having a crystal structure of 100 parts by weight. When the amount of the inorganic filler is located within the above-described range, the obtained resin component can be avoided from being brittle.

The suppression of hydrolysis of polyester is important in view of reliability for a long period in use of the moldings. Accordingly, a hydrolysis inhibitor is further preferably added to the resin component according to the present invention. As such a hydrolysis inhibitor, any of hydrolysis inhibitors that can suppress the hydrolysis of the biodegradable resin may be used without special limitation. For example, compounds having reactivity with active hydrogen in the biodegradable resin may be exemplified. The above-described compound is added to the biodegradable resin to reduce the amount of active hydrogen in the biodegradable resin, so that the active hydrogen can be prevented from hydrolyzing polymer chains forming the biodegradable resin like a catalyst. Here, the active hydrogen indicates hydrogen in the bond of oxygen, nitrogen, etc. with hydrogen (N—H bond or O—H bond). This hydrogen has reactivity higher than that of hydrogen in the bond of carbon and hydrogen (C—H bond). More specifically, for instance, hydrogen in a carboxyl group: —COOH, hydroxyl group: —OH, an amino group: —NH2, an amide bond: —NHCO— etc. in the biodegradable resin may be exemplified.

As the hydrolysis inhibitor, for example, carbodiimide compounds, isocyanate compounds or oxazoline compounds may be applied thereto. Especially, since the carbodiimide compound can be melted and kneaded with a biodegradable polymer compound and can more suppress the hydrolysis of the biodegradable resin with a small amount of addition, the carbodiimide compound is preferable.

The carbodiimide compound is a compound having one or more carbodiimide groups in a molecule and includes a polycarbodiimide compound. As monocarbodiimide compounds included in the carbodiimide compounds, dicyclohexyl carbodiimide, diisopropyl carbodiimide, dimethyl carbodiimide, diisobutyl carbodiimide, dioctyl carbodiimide, diphenyl carbodiimide, naphthyl carbodiimide, etc. may be exemplified. Dicyclohexyl carbodiimide or diisopropyl carbodiimide that is especially industrially available is preferable among them.

As the isocyanate compounds, for example, 2,4-tolylene diisocyanate, 2,6-tolylene diisocyanate, m-phenylene diisocyanate, p-phenylene diisocyanate, 4,4'-diphenyl methane diisocyanate, 2,4'-diphenyl methane diisocyanate, 2,2'-diphenyl methane diisocyanate, 3,3'-dimethyl-4,4'-biphenylene diisocyanate, 3,3'-dimethoxy-4,4'-biphenylene diisocyanate, 3,3'-dichloro-4,4'-biphenylene diisocyanate, 1,5-naphthalene diisocyanate, 1,5-tetrahydro naphthalene diisocyanate, tetramethylene diisocyanate, 1,6-hexamethylene diisocyanate, dodecamethylene diisocyanate, trimethyl hexamethylene diisocyanate, 1,3-cyclohexylene diisocyanate, 1,4-cyclohexylene diisocyanate, xylylene diisocyanate, tetramethyl xylylene diisocyanate, hydrogenated xylylene diisocyanate, lysine diisocyanate, isophorone diisocyanate, 4,4'-dicyclohexyl methane diisocyanate, 3,3'-dimethyl-4,4'-dicyclohexyl methane diisocyanate, etc. may be exemplified.

As the oxazoline compounds, for example, 2,2'-o-phenylene bis (2-oxazoline), 2,2'-m-phenylene bis(2-oxazoline), 2,2'-p-phenylene bis (2-oxazoline), 2,2'-p-phenylene bis(4-methyl-2-oxazoline), 2,2'-m-phenylene bis (4-methyl-2-oxazoline), 2,2'-p-phenylene bis(4,4'-dimethyl-2-oxazoline), 2,2'-m-phenylene bis(4,4'-dimethyl-2-oxazoline), 2,2'-ethylene bis(2-oxazoline), 2,2'-tetramethylene bis(2-oxazoline), 2,2'-hexamethylene bis(2-oxazoline), 2,2'-octamethylene bis (2-oxazoline), 2,2'-ethylene bis(4-methyl-2-oxazoline), 2,2'-diphenylene bis(2-oxazoline), etc. may be exemplified.

The above-described hydrolysis inhibitors can be easily produced in accordance with well-known methods and marketed products may be suitably employed.

Since the biodegradation speed of the resin component of the present invention can be adjusted depending on the kinds or the amount of addition of the hydrolysis inhibitor used in the present invention, the kind and a quantity of mixing of the hydrolysis inhibitor to be mixed may be determined in accordance with a desired product. Specifically, the amount of addition of the hydrolysis inhibitor is about 5 wt % or lower relative to all the weight of the resin component and preferably about 1 wt %. Further, as the hydrolysis inhibitor, the above-described compounds may be independently used or two or more kinds of compounds may be used together.

To the resin component according to the present invention, various kinds of conventionally well-known addition agents such as an antioxidant, an optical stabilizer, an ultraviolet absorbent, a pigment, a colorant, an antistatic agent, a mold releasing agent, perfume, lubricant, a flame retardant, a filler, an antibacterial or antifungal agent, etc. may be added as desired so as not to seriously interfere with a crystallization or a crystalline property.

The resin component according to the present invention is produced in such a way that the above-described cyclic compounds or the mixture thereof, polyester capable of having the crystal structure and further other constituents are mixed together as desired. As a more preferable method for producing the resin component according to the present invention from the respective constituents as raw materials thereof, a method that the biodegradable resin as a raw material is mixed with the inorganic filler, the hydrolysis inhibitor or the like as desired and the mixture was melted and kneaded by using an extruder is exemplified. As a method for producing the resin component as well as the above-described method, what is called a solution method may be employed. Here, the solution method is a method that arbitrary solution capable of dispersing and dissolving the respective constituents is used to completely agitate the constituents as raw materials and solvent, form slurry and dry and removed the solvent. The method for producing the resin component according to the present invention is not limited to these methods and conventionally well-known methods except these methods may be employed.

In the present invention, the cyclic compound is preferably uniformly and finely dispersed in the biodegradable polyester. A conventionally well-known method may be employed for the uniform dispersion. For example, a method for dispersing pigment in the resin and coloring the resin may be used. For example, a method that three rolls are used may be exemplified. Otherwise, a method that simple heating and kneading operations are repeated a plurality of times is also exemplified.

In the present invention, the mixing ratio of the cyclic compound in the resin component is preferably located within a range of about 0.001 to 10 parts by weight relative to the polyester capable of having the crystal structure of 100 parts by weight and more preferably located within a range of about 0.01 to 1 parts by weight. Further, in the present invention, the crystallization rate of the resin component is preferably located within a range of about 40 to 100%. Further, the crystallization time of the resin component is preferably located within a range of about 0 to 200 seconds. The modulus of elasticity of the resin component at 80° C. is preferably located within a range of about 50 to 5000 MPa. The crystallization rate and the crystallization time are respectively obtained by referring to below-described Examples. The modulus of elasticity is obtained by the same method as the above-described measuring method. Accordingly, a detailed explanation thereof is omitted.

The resin component can be also widely applied to various kinds of moldings similar to those of the above-described resin component. That is, since the crystalline property of the resin component is high, the moldings composed of the resin component according to the present invention are excellent in rigidity and sometimes high in transparency as described above. Accordingly, the moldings are preferably suitably used as products in which the rigidity and transparency are highly requested.

Now, some specific Examples of the resin component according to the present invention will be described.

EXAMPLE 1

In this example 1, as polyester capable of having a crystal structure, H100J (produced by Mitsui Chemicals, Inc.) as polylactic acid was used. The polylactic acid had molecular weight of 200,000.

As a cyclic compound serving as a nucleus agent, Pigment Yellow 109 (produced by Chiba Fine Chemical Co., Ltd. IRGAZIN Yellow 2GLTE) was employed. The specific surface area thereof was 30 $m^2/g$.

The nucleus agent was mixed with the polylactic acid so as to have 0.5 parts by weight relative to the polylactic acid of 100 parts by weight. The mixture was heated and kneaded, and then, pelletized to obtain a resin component for molding of the Example 1.

The crystalline property of this resin component for molding was evaluated by a differential scanning calorimetry (DSC) in accordance with a method disclosed in Japanese Patent Application Laid-Open No. hei 10-158369. A sample of 3 to 4 mg was cut from a pellet and accommodated in an aluminum pan. The sample was temporarily heated to 200° C. and cooled to 0° C. at 50° C./minute, and then, the temperature of the sample was raised at 20° C./minute to carry out a measurement. A crystallization rate defined by a following formula was obtained from a heat generation rate due to crystallization at about 100° C. and a heat absorption rate due to melting at about 160° C.

Crystallization rate(%)=(1−heat generation rate of crystallization/heat absorption rate of melting)×100

Further, the general crystallization speed (crystallization time) was measured under a photographing operation by a polarizing microscope. A small amount of resin component was mounted on a thin glass (about 0.1 mm), heated by a hot stage at 200° C., and further pressed and covered by a thin glass to have a sample to be observed. The temperature of the sample heated to 200° C. was lowered at 90° C./minute and held and crystallized at 120° C. The state thereof was observed by a crossed nicol. Since the crystal of polylactic acid has a double refraction, the growth of the crystal can be observed by the crossed nicol. As the crystal grows, a visual field to be observed gradually becomes light and the brightness of the visual field to be observed is saturated at a prescribed level.

The image of the visual field to be observed was recorded by an objective lens of 10 times and a black and white ⅓ inch CCD video camera and a range of about 600×450 μm was recorded (digitizing by 10 bits of about 640×480 pixels) and taken in an image capture board of a personal computer. Then, the average of the brightness of an area of about 378×283 μm in the center of the visual field was obtained (refer simply it to as brightness, hereinafter). The obtained average of brightness was plotted relative time. The time at 120° C. was determined to be 0 and a reference. Since the double refraction of the crystal is used, it is important to recognize many spherulites in all the visual field to be observed as observing conditions. When the number of spherulites is small within the visual field to be observed (when magnification is high or an area set for calculating the average brightness is small), the change of brightness may be possibly uneven relative to the time.

Crystallization time was obtained as described below. That is, as shown in FIG. 1, the leading edge of the brightness in the vicinity of ½ as high as saturation is extrapolated 1 by a straight line. Further, a saturation level is horizontally extrapolated 2 by a straight line. The time 4 at the intersection of them is read to obtain the crystallization time 3.

The crystallization rate and the crystallization time of the resin component obtained in this Example which are obtained by the above-described methods are shown in Table 1.

EXAMPLE 2

In this example 2, as polyester capable of having a crystal structure, H100J (produced by Mitsui Chemicals, Inc.) as polylactic acid was used. The polylactic acid had molecular weight of 200,000.

As a cyclic compound, Pigment Yellow 110 (produced by Chiba Fine Chemical Co., Ltd. CROMOPHTAL Yellow 2RLP) was employed. The specific surface area thereof was 49 $m^2/g$.

A nucleus agent was mixed with the polylactic acid so as to have 0.5 parts by weight relative to the polylactic acid of 100 parts by weight. The mixture was heated and kneaded, and then, pelletized to obtain a resin component for molding of the Example 2.

The resin component was evaluated in the same manner as that of the Example 1, and the results thereof are shown in the following Table 1.

COMPARATIVE EXAMPLE 1

In a Comparative Example 1, the above-described H100J was used as polylactic acid and the polylactic acid was subjected to producing processes under the same conditions as those of the previous Examples. That is, the polylactic acid was heated and kneaded and pelletized to obtain a resin component composed of only the polylactic acid. The resin component was evaluated in the same manner as described above. The results thereof are shown in the following Table 1.

COMPARATIVE EXAMPLE 2

In a Comparative Example 2, a resin component including polylactic acid of 100 parts by weight and calcium stearate (produced by Kanto Kagaku) of 0.5 parts by weight was likewise produced. The resin component was evaluated in the same manner as described above. The results thereof are shown in Table 1.

As a result, it is said that the salt of a long chain carboxylic acid has an effect as a nucleus agent relative to polylactic acid. Accordingly, the crystallization rate was certainly slightly improved.

COMPARATIVE EXAMPLE 3

In a Comparative Example 3, a resin component including polylactic acid of 100 parts by weight and bis(p-methyl benzylidene) sorbitol (produced by New Japan Chemical Co., Ltd. Gel All MD) of 0.5 parts by weight was likewise produced. The resin component was evaluated in the same manner as described above. The results thereof are shown in the following Table 1.

TABLE 1

|  |  | Biodegradable Resin (Parts by Weight) |  | Addition Material (Parts by Weight) |  |
|---|---|---|---|---|---|
| Example | 1 | Polylactic Acid H100J | 100 | IRGAZIN Yellow 2DLTE | 0.5 |
|  | 2 | Polylactic Acid H100J | 100 | CROMOPHTAL Yellow 2RLP | 0.5 |
| Comparative Example | 1 | Polylactic Acid H100J | 100 | No | No |
|  | 2 | Polylactic Acid H100J | 100 | Calcium Stearate | 0.5 |
|  | 3 | Polylactic Acid H100J | 100 | Bis(p-Methyl benzylidene) sorbitol | 0.5 |

|  |  | Crystallization Rate (%) | Crystallization Time (sec) |
|---|---|---|---|
| Example | 1 | 100 | 27 |
|  | 2 | 100 | 28 |
| Comparative Example | 1 | 7 | 237 |
|  | 2 | 12 | 207 |
|  | 3 | 7 | 212 |

Bis (p-methyl benzylidene) sorbitol is proposed as a nucleus agent in the prior art. However, the effect thereof was extremely low under a series of evaluations of this time.

When the amount of addition was 2 parts by weight, an obvious effect was not found.

Now, some specific Examples of another resin component according to the present invention will be described.

EXAMPLE 3

In an Example 3, as polyester capable of having a crystal structure, H100J (produced by Mitsui Chemicals, Inc.) as polylactic acid was used. The polylactic acid had molecular weight of 200,000.

As a cyclic compound serving as a nucleus agent, Pigment Blue 15:3 (produced by Chiba Fine Chemical Co., Ltd. IRGALITE Blue GBP) was employed.

The nucleus agent was mixed with the polylactic acid so as to have 0.5 parts by weight relative to the polylactic acid of 100 parts by weight. The mixture was heated and kneaded, and then, pelletized to have a resin component for molding of Example 3A. Resin components for molding of Examples 3B and 3C including the nucleus agent of 0.1 parts by weight and 0.05 parts by weight were obtained.

The crystalline property of the resin component for molding was evaluated by a differential scanning calorimetry (DSC) in accordance with a method disclosed in Japanese Patent Application Laid-Open No. hei 10-158369. A sample of 3 to 4 mg was cut from a pellet and accommodated in an aluminum pan. The sample was temporarily heated to 200° C. and cooled to 0° C. at 50° C./minute, and then, the temperature of the sample was raised at 20° C./minute to carry out a measurement. A crystallization rate defined by a following formula was obtained from a heat generation rate due to crystallization at about 100° C. and a heat absorption rate due to melting at about 160° C.

Crystallization rate(%)=(1−heat generation rate of crystallization/heat absorption rate of melting)×100

In the case of a crystalline resin, when the crystallization speed is increased, the molding time upon injection molding can be shortened. Accordingly, productivity can be enhanced and a production cost can be improved. Further, in case the crystallization time is the same, when the crystallization speed is high, the moldings whose crystallization is higher can be produced and rigidity can be improved.

As an index showing the improvement of such moldability, the general crystallization speed (crystallization time) was measured under a photographing operation by a polarizing microscope. A small amount of resin component was mounted on a thin glass (about 0.1 mm), heated by a hot stage at 200° C., and further covered with a thin glass in a sandwiched state to have a sample to be observed. At this time, a metallic ring of 0.1 mm was used as a spacer between the glasses as desired. The temperature of the sample heated to 200° C. was lowered at 90° C./minute and held and crystallized at 120° C. The state thereof was observed by a crossed nicol. Since the crystal of polylactic acid has a double refraction, the growth of the crystal can be observed by the crossed nicol. As the crystal grows, a visual field to be observed gradually becomes light and the brightness of the visual field to be observed is saturated at a prescribed level.

The image of the visual field to be observed was recorded by an objective lens of 10 times and a black and white ⅓ inch CCD video camera and a range of about 600×450 μm was recorded (digitizing by 10 bits of about 640×480 pixels) and taken in an image capture board of a personal computer. Then, the average of the brightness of an area of about 378×283 μm in the center of the visual field was obtained (refer simply it to as brightness, hereinafter). The obtained average of brightness was plotted relative time. The time at 120° C. was determined to be 0 and a reference. Since the double refraction of the crystal is used, it is important to recognize many spherulites in all the visual field to be observed as observing conditions. When the number of spherulites is small within the visual field to be observed (when magnification is high or an area set for calculating the average brightness is small), the change of brightness may be possibly uneven relative to the time.

Crystallization time was obtained as described below. That is, as shown in FIG. 1, the leading edge of the brightness in the vicinity of ½ as high as saturation is extrapolated 1 by a straight line. Further, a saturation level is horizontally extrapolated 2 by a straight line. The time 4 at the intersection of them is read to obtain the crystallization time 3.

The crystallization rate and the crystallization time of the resin component obtained in the Example 3, which are obtained by the above-described methods are shown in following Table 2.

EXAMPLE 4

In an Example 4, a resin component for molding was obtained in the same manner as that of the Example 3A except that Pigment Blue 15 (produced by Chiba Fine Chemical Co., Ltd, IRGARITE Blue BLPO) of 0.5 parts by weight was used in place of IRGARITE Blue GBP of 0.5 parts by weight in the Example 3A.

EXAMPLE 5

In an Example 5, a resin component for molding was obtained in the same manner as that of the Example 3A except that Pigment Blue 15:6 (produced by Dainippon Ink and Chemicals Incorporated, FASTROGEN Blue EP-7) of 0.5 parts by weight was used in place of IRGARITE Blue GBP of 0.5 parts by weight in the Example 3A. Comparative Example 4

In a Comparative Example 4, the above-described H100J was used as polylactic acid and the polylactic acid was subjected to producing processes under the same conditions as those of the Examples 3 to 5. That is, the polylactic acid was heated and kneaded and pelletized to obtain a resin component composed of only the polylactic acid. The resin component was evaluated in the same manner as described above. The results thereof are shown in the following Table 2.

COMPARATIVE EXAMPLE 5

In a Comparative Example 5, a resin component including polylactic acid of 100 parts by weight and calcium stearate (produced by Kanto Kagaku) of 0.5 parts by weight was likewise produced. The resin component was evaluated in the same manner as described above. The results thereof are shown in the Table 2.

As a result, it is said that the salt of a long chain carboxylic acid has an effect as a nucleus agent relative to polylactic acid. Accordingly, the crystallization rate was assuredly slightly improved.

COMPARATIVE EXAMPLE 6

A resin component including polylactic acid of 100 parts by weight and bis(p-methyl benzylidene) sorbitol (produced by New Japan Chemical Co., Ltd. Gel All MD) of 0.5 parts by weight was likewise produced. The resin component was evaluated in the same manner as described above. The results thereof are shown in the following Table 2.

Bis (p-methyl benzylidene) sorbitol is proposed as a nucleus agent in the prior art. However, the effect thereof was extremely low under a series of evaluations of this time.

When the amount of addition was 2 parts by weight, an obvious effect was not found.

TABLE 2

| | | Biodegradable Resin (Parts by Weight) | | Addition Material (Parts by Weight) | |
|---|---|---|---|---|---|
| Example | 3A | Polylactic Acid H100J | 100 | IRGARITE Blue GBP | 0.5 |
| | 3B | Polylactic Acid H100J | 100 | IRGARITE Blue GBP | 0.5 |
| | 3C | Polylactic Acid H100J | 100 | IRGARITE Blue GBP | 0.05 |
| | 4 | Polylactic Acid H100J | 100 | IRGARITE Blue GLPO | 0.5 |
| | 5 | Polylactic Acid H100J | 100 | FASTROGEN Blue EP-7 | 0.5 |
| Comparative Example | 4 | Polylactic Acid H100J | 100 | No | No |
| | 5 | Polylactic Acid H100J | 100 | Calcium Stearate | 0.5 |
| | 6 | Polylactic Acid H100J | 100 | Bis(p-Methyl benzylidene) sorbitol | 0.5 |

| | | Crystallization Rate (%) | Crystallization Time (sec) |
|---|---|---|---|
| Example | 3A | 100 | 25 |
| | 3B | 100 | 37 |
| | 3C | 100 | 47 |
| | 4 | 38 | 82 |
| | 5 | 92 | 42 |
| Comparative Example | 4 | 7 | 237 |
| | 5 | 12 | 207 |
| | 6 | 7 | 212 |

The present invention is not limited to the above-described embodiments or Examples explained by referring to the drawing. It is apparent for a person with ordinary skill in the art that various changes, substitutions or equivalence thereto can be made without departing attached claims and the gist thereof.

INDUSTRIAL APPLICABILITY

Since a resin component according to the present invention has a high degree of crystallization, the resin component is excellent in its rigidity and moldability. In the resin component according to the present invention, a transparency can be improved, the resin component can be applied to a wide range. Further, since the resin component according to the present invention is decomposed in a natural environment after its disposal, the resin component is also preferable in view of global atmospheric maintenance.

The invention claimed is:

1. A molding made of a resin component comprising: a cyclic compound in the amount of 0.001 to 10 parts by weight, and a polylactic acid polyester capable of having a crystal structure of 100 parts by weight wherein, the cyclic compound is 3,3'-(2-methyl-1,3-phenylene) diimino-bis-4,5,6,7-tetrachloro-1H-isoindole-1-one or 3,3'-(1,4-phenylene diimino) bis-4,5,6,7-tetrachloro-1H-isoindole-1-one.

2. The molding according to claim 1, wherein the molding is a casing for casings of electric and electronic devices.

3. A method for producing a resin component comprising the steps of:

mixing a cyclic compound represented by the following formula:

A1-B-A2 with a polylactic acid polyester capable of having a crystal structure of 100 parts by weight; and heating and kneading the mixture, wherein, A1 and A2 are the same or different and represented by the compound below

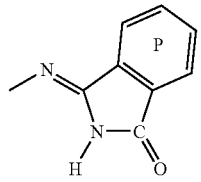

B is a bivalent hydrocarbon group which may include at least one substituent 1 selected from a group of substituents X, P is a benzene ring which may include at least one substituent 2 selected from the group of substituents X, the cyclic compound is in the amount of 0.001 to 10 parts by weight, the substituents 1 and 2 can be the same or different, the group of substituents X consists of halogen atoms, nitro groups, cyano groups, hydroxy groups, thiol groups, sulfo groups, sulfino groups, mercapto groups, phosphono groups, alkyl groups, hydroxy alkyl groups, halogenoalkyl groups, cycloalkyl groups, alkenyl groups, cycloalkenyl groups, oxo groups, thioxo groups, amidino groups, imino groups, alkylenedioxy groups, alkoxy groups, alkylthio groups, alkanoyloxy groups, alkoxy carbonyl groups, aralkyloxy carbonyl groups, thiocarbamoyl groups, alkyl sulfinyl groups, alkyl sulfonyl groups, sulfamoyl groups, mono-alkyl sulfamoyl groups, di-alkyl sulfamoyl groups, allyl sulfamoyl groups, allyloxy groups, allylthio groups, allyl sulfinyl groups, allyl sulfonyl groups, allyl carbonyl groups, allyl carbonyloxy groups, alkyl carbonyl amino groups, halogenated alkyl carbonyl amino groups, carbamoyl groups, amino groups ureido groups, carboxamide groups, sulfonamide groups, and heterocyclic groups.

4. A molding composed of a resin component comprising: one or more cyclic compounds selected from (a) a copper phthalocyanine crystal which may include at least one substituent 3 selected from a group of substituents Y, (b) a phthalocyanine compound which may include one kind of a metal and which may include at least one substituent 5 selected from the group of substituents Y, and (c) a porphyrin compound (c) which may include at least one substituent 5 selected from the group of substituents Y; and a polylactic acid polyester capable of having a crystal structure of 100 parts by weight, wherein, the substituents 3, 4 and 5 can be the same or different, the group of substituents Y consists of halogen atoms, nitro groups, cyano groups, hydroxy groups, thiol groups, sulfo groups, sulfino groups, mercapto groups, phosphono groups, alkyl groups, hydroxy alkyl groups, halogeno alkyl groups, cycloalkyl groups, alkenyl groups, cycloalkenyl groups, alkynyl groups, oxo groups, thioxo groups, amidino groups, imino groups, alkylenedioxy groups, hydrocarbon groups, alkoxy groups, alkythio groups, carboxyl groups, alkanoyl groups, alkanoyloxy groups, alkoxy carbonyl groups, aralkyloxy carbonyl groups, thiocarbamoyl groups, sulfinyl groups, alkyl sulfonyl groups, sulfamoyl groups, mono-alkyl sulfamoyl groups, di-alkyl sulfamoyl groups, allyl groups, allyloxy groups, allylthio groups, allyl sulfinyl groups, allyl sulfonyl groups, allyl carbonyl groups, allyl carbonlyoxy groups, alkyl carbonyl amino groups, halogenated alkyl carbonyl amino groups, carbamoyl groups, amino groups, ureido groups, carboxamide groups, sulfonamide groups, hydroxyl groups, heterocylic groups and aromatic heterocyclic groups, and the metal is selected from a group consisting of zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium.

5. The molding according to claim 4, wherein the molding is a casing for electric or electronic devices.

6. A method for producing a resin component comprising the steps of:

mixing one or more cyclic compounds selected from a group consisting of (a) a copper phthalocyanine crystal which may include a substituent group 3 selected from a group of substituents Y, (b) a phthalocyanine compound which may include one kind of metal and which may include at least one substituent group 4 selected from the group of substituents Y and (c) a porphyrin compound which may include at least one substituent group 5 selected from the group of substituents Y with a polylactic acid polyester capable of having a crystal structure of 100 parts by weight; and heating and kneading the mixture, wherein, the substituent groups 3, 4 and 5 can be the same or different substituent groups, the group of substituents Y consists of halogen atoms, nitro groups, cyano groups, hydroxy groups, thiol groups, sulfo groups, sulfino groups, mercapto groups, phosphono groups, alkyl groups, hydroxy alkyl groups, halogeno alkyl groups, cycloalkyl groups, alkenyl groups, cycloalkenyl groups, alkynyl groups, oxo groups, thioxo groups, amidino groups, imino groups, alkylenedioxy groups, hydrocarbon groups, alkoxy groups, alkythio groups, carboxyl groups, alkanoyl groups, alkanoyloxy groups, alkoxy carbonyl groups, aralkyloxy carbonyl groups, thiocarbamoyl groups, sulfinyl groups, alkyl sulfonyl groups, sulfamoyl groups, mono-alkyl sulfamoyl groups, di-alkyl sulfamoyl groups, allyl groups, allyloxy groups, allylthio groups, allyl sulfinyl groups, allyl sulfonyl groups, allyl carbonyl groups, allyl carbonlyoxy groups, alkyl carbonyl amino groups, halogenated alkyl carbonyl amino groups, carbamoyl groups, amino groups, ureido groups, carboxamide groups, sulfonamide groups, hydroxyl groups, heterocylic groups and aromatic heterocyclic groups, and the metal is selected from a group consisting of zinc, cadmium, mercury, aluminum, germanium, gallium, indium, thallium, tin, lead, antimony, bismuth, lithium, sodium, potassium, rubidium, cesium, beryllium, magnesium, calcium, strontium, barium, scandium, yttrium, lanthanum, titanium, zirconium, hafnium, vanadium, niobium, tantalum, chromium, molybdenum, tungsten, manganese, technetium, rhenium, iron, ruthenium, osmium, cobalt, rhodium, iridium, nickel, palladium, platinum, copper, silver, gold, silicon and cerium.

* * * * *